(12) United States Patent
Guo

(10) Patent No.: US 8,076,082 B2
(45) Date of Patent: Dec. 13, 2011

(54) METHODS FOR IDENTIFYING MULTIPLE DNA ALTERATION MARKERS IN A LARGE BACKGROUND OF WILD-TYPE DNA

(75) Inventor: Baochuan Guo, Solon, OH (US)

(73) Assignee: Cleveland State University, Cleveland, OH (US)

( * ) Notice: Subject to any disclaimer, the term of this patent is extended or adjusted under 35 U.S.C. 154(b) by 218 days.

(21) Appl. No.: 12/090,147

(22) PCT Filed: Oct. 13, 2006

(86) PCT No.: PCT/US2006/040357
§ 371 (c)(1),
(2), (4) Date: Sep. 29, 2008

(87) PCT Pub. No.: WO2007/047572
PCT Pub. Date: Apr. 26, 2007

(65) Prior Publication Data
US 2009/0042196 A1    Feb. 12, 2009

Related U.S. Application Data

(60) Provisional application No. 60/727,168, filed on Oct. 14, 2005.

(51) Int. Cl.
*C12Q 1/68* (2006.01)
*C12P 19/34* (2006.01)

(52) U.S. Cl. .................................... 435/6.12; 435/91.2
(58) Field of Classification Search .................. 435/91.2, 435/6, 6.12
See application file for complete search history.

(56) References Cited

U.S. PATENT DOCUMENTS

| | | | |
|---|---|---|---|
| 5,834,181 A * | 11/1998 | Shuber | 435/5 |
| 2003/0119005 A1 | 6/2003 | Brush et al. | |
| 2003/0143584 A1 | 7/2003 | Li-Sucholeiki | |
| 2005/0227265 A1 | 10/2005 | Barany et al. | |

FOREIGN PATENT DOCUMENTS

| WO | WO 03/006677 A | 1/2003 |
|---|---|---|
| WO | WO 2004/081191 A | 9/2004 |

OTHER PUBLICATIONS

Sun, X. et al., "Detection of Tumor Mutations in the Presence of Excess Amounts of Normal DNA" Nature Biotechnology, vol. 19, pp. 186-189, Feb. 2002.
International Search Report for International Application No. PCT/US2006/040357, Sep. 2007.
Jeffreys, Alec J. et al.: "DNA Enrichment by Allele-Specific Hybridization (DEASH): A Novel Method for Haplotyping and for Detecting Low-Frequency Base Substitutional Variants and Recombinant DNA Molecules." Genome Research, vol. 13, No. 10. Oct. 2003, pp. 2316-2324, XP-002553628 ISSN: 1088-9051.
Sun, Xiyuan et al.: "Detection of Mononucleotide Repeat Sequence Alterations in a Large Background of Normal DNA for Screening High-Frequency Microsatellite Instability Cancers." Clinical Cancer Research, The American Association for Cancer Research, US, vol. 12, No. 2, Jan. 15, 2006, pp. 454-459, XP-002429105 ISSN: 1078-0432.
Supplementary European Search Report for Application No. EP 06 81 6985, Dec. 2009.

* cited by examiner

*Primary Examiner* — Kenneth R. Horlick
*Assistant Examiner* — Joyce Tung
(74) *Attorney, Agent, or Firm* — Fay Sharpe LLP

(57) ABSTRACT

Methods for simultaneously surveying the status of a large number of DNA mutation markers are described. In addition, methods for simultaneously determining the methylation status at multiple sites of a collection of genes, in a single assay, are described.

43 Claims, 11 Drawing Sheets

METHODS FOR IDENTIFYING MULTIPLE DNA ALTERATION MARKERS IN A LARGE BACKGROUND OF WILD-TYPE DNA

CROSS REFERENCES TO RELATED APPLICATIONS

This application claims priority from U.S. provisional application Ser. No. 60/727,168 filed Oct. 14, 2005. U.S. provisional application Ser. No. 60/727,168 is also incorporated herein by reference.

BACKGROUND

Despite the latest advances in imaging technology, cancer is still often diagnosed after metastasis has occurred. Needless deaths from cancer occur as a consequence of detection after metastasis. Therefore, detection of cancer prior to metastasis is an urgent social priority.

An approach for such early detection is molecular testing. Molecular testing, in which molecular markers are used to detect cancer, is emerging as an attractive method for cancer screening due to its ability to allow physicians to detect cancer at the earliest stage by analysis of a single drop of bodily fluid or a small stool sample.

DNA mutation and aberrant methylation of genes are among the most common DNA alteration events leading to the development of cancer. For example, mutations in the gene p53 occur in approximately 50-60% of all cancers. Aberrant methylation of genes is found in many types of cancers. Hence, DNA mutation and methylation serve as cancer indicators or markers and thus if identified, can be used to diagnose cancer. Because of this, efforts have been made to develop DNA-based assays to screen cancer. For example, fecal DNA testing based on mutation analysis of several genes was developed for colorectal cancer (CRC) screening. Similarly, fecal DNA testing based on methylation analysis has also been used to screen for colorectal cancer.

Despite use as a cancer indicator, mutation analysis remains a technical challenge when applied to screening. This is due to two reasons. First, detection of mutations in clinical samples requires methods that are highly sensitive. Since clinical specimens comprise a minority of mutated sequences (often less than 1%) in a vast excess of wild-type sequences, only highly sensitive assays can be used. Furthermore, cancer can result from different pathways involving the accumulation of mutations in different genes and thus no single mutation event can serve as a reliable indicator of cancer. As a consequence, a panel or collection of genes must be used to detect cancer. For example, fecal DNA testing utilizes mutations in k-ras, p53, APC, and BAT26 as markers to detect colorectal cancer. Moreover, mutations in a gene often occur in different bases. For example, the APC mutations can occur anywhere within its first 1600 codons. Thus, a clinical test must be able to survey the mutation status of a large number of markers in a vast excess population of wild-type DNA.

Second, cancer screening must be cost-effective, since this factor eventually determines the extent to which such method is used in health care intervention. Fecal occult testing is a good example. Fecal occult testing is not particularly sensitive, but is more cost-effective than other methods. As a result, fecal occult testing is the method recommended by the U.S. Preventive Services Task Force for CRC screening. It is virtually impossible for medical policy makers and/or insurance companies to embrace a screening test that is not cost-effective. Thus, a good clinical screening test must be cost-effective in addition to providing a reasonable degree of sensitivity.

A number of methods have been employed to detect mutations. In general, these methods can be classified into two groups. In one set of methods, polymerase chain reaction (PCR) is a component of the detection system. These methods rely on the selective amplification of mutant alleles and allow the sensitive detection of mutant alleles in a great excess population of wild-type alleles. Allele-Specific-Amplification (ASA) and Mutant Enriched PCR (ME-PCR) are two widely used methods for this application, both of which can detect mutant DNA in an excess of wild-type DNA having a population 100,000 times greater than that of the mutant DNA. However, these methods enrich mutant DNA by PCR and each PCR reaction generally detects one mutation. As previously noted, a large panel of mutations must be utilized to attain high screening sensitivity. Therefore, a number of PCR reactions would be needed if this set of methods is used for cancer screening, thereby increasing the screening cost. Hence, assays employing this set of methods may not be cost-effective, and thus would not be suitable for clinical screening.

In the second set of methods, mutations are analyzed after the target sequence has been amplified by PCR. Mutations can then be analyzed using technologies such as sequencing, DHPLC, DNA microarray, DGGE, and SSCP. Unlike the first set of methods, the second set of methods can survey the mutations within a long sequence span. However, these methods are not sufficiently sensitive to detect mutations in a large background of wild-type DNA. As a result, although this group of methods has been routinely used to detect mutations in DNA derived from dissected tumor samples where the abundance of mutant DNA is relatively high, the poor sensitivity of this set of methods has generally impeded their use to detect mutations in DNA derived from clinical specimens such as bodily fluids and stool, where the abundance of mutant DNA is low. Hence, the second set of methods is also not suitable for clinical screening because of their poor sensitivity.

Recently, a PCR/ligase detection reaction (LDR) method for mutation analysis has been proposed, which combines polymerase chain reaction/ligase detection reaction with DNA microarray. A feature of this method is that it can survey the mutation status of a number of markers and it has been used to detect mutations in DNA derived from clinical specimens. However, this method has limitations. Although high sensitivity was reported with a single mutation system, it remains a challenge to attain a high sensitivity when PCR/LDR is used to survey hundreds of mutations. This is because LDR may not be equally sensitive for all sequences, as it relies on the ability of ligase to distinguish different sequences. More importantly, amplification by PCR varies greatly from sequence to sequence and thus some mutations may not be detectable in a multiplexed setting. Thus, it is a challenge to detect mutations if their sequences are poorly amplified in multiplexed PCR.

Clearly, there is an urgent need in the art for analysis of the status of a large panel of DNA mutation markers in a large background of wild-type DNA in a sensitive and cost-effective manner.

As previously noted, aberrant methylation of genes is a DNA alteration event that frequently leads to cancer. Methylation refers to the biochemical addition of a methyl group ($-CH_3$) to a biological molecule. Aberrant methylation of CpG dinucleotides in the 5' regulatory region of genes is a common event leading to gene silence. As a result of CpG island hypermethylation, chromatin structure in the promoter can be altered, thereby preventing normal interaction with the transcriptional machinery. It is now clear that aberrant methylation is a widespread phenomenon in cancer. If this occurs in genes critical to growth inhibition, the resulting silencing of transcription could promote tumor progression. Thus, like mutation, promoter CpG island hypermethylation is a common mechanism for transcriptional inactivation of tumor suppressor genes. There has been considerable interest in methylation analysis, as methylation analysis can not only yield insights into cancer, but this analysis may also lead to the discovery of therapeutic and diagnostic biomarkers. Recently, monitoring global changes in DNA methylation has been applied to molecular classification of cancer. More recently, it was found that methylation was associated with response to cancer treatment. Therefore, methylation markers can also be used to classify and predict types and stages of cancer, cancer therapeutic outcomes, and survival.

Methylation analysis is a key to the characterization of DNA methylation. Despite its importance, however, methylation analysis remains a technical challenge, especially when biospecimens are analyzed. This is due to two issues. The first one is sensitivity. The methods for analysis of clinical samples must be sensitive, as biospecimens are heterogeneous and often comprise minority methylated sequences in an excess of unmethylated sequences. For example, tissue specimens such as paraffin-embedded samples may contain as little as 1% of altered DNA and their abundance is even lower in other clinical biospecimens such as bodily fluids, blood, urine, and stool. Thus, only highly sensitive assays can reveal methylation in a vast excess of unmethylated DNA.

The second issue relating to methylation analysis being a technical challenge is multiplexing capability. Cancer results from different pathways involving accumulation of methylation in many genes and no single methylation event can provide an accurate indicator for cancer analysis. As a result, a large panel of genes must be profiled to characterize the association of methylation with cancer. Hence, technologies for methylation analysis should also have high-order multiplexing capability. In addition, the number of altered DNA molecules is limited in clinical specimens. This is a problem especially for methylation analysis as only 10-20% of the DNA molecules can be recovered after bisulfite treatment. Hence, multiplexing capability is essential to methylation analysis as there are insufficient amounts of altered DNA molecules in clinical biospecimens to allow the analysis of one gene at a time.

Methylation analysis can profile methylation globally, identify methylation patterns at a cluster of CpG sites or genes, and determine methylation levels at individual CpG sites. Methylation-restriction enzyme digestion is a good method for methylation analysis, but most of the currently used methods are based on bisulfite treatment which can convert cytosine to uracil whereas the methylated cytosine residues are unaltered. The treated DNA is then amplified by PCR with specific primers to yield fragments in which all uracil residues are converted to thymine. As a result of the differences in the sequences of methylated and unmethylated DNA created by bisulfite treatment, the methylation status at a CpG site can be determined using a conventional mutation analysis method. Thus, the methylation status of a CpG site can be determined by a mutation analysis method after bisulfite treatment.

Current bisulfite-based methods for methylation analysis can be classified into three approaches. The first approach is bisulfite-based sequencing that can map methylated cytosine residues within a gene promoter. Its advantage is that it identifies every methylated cytosine within a gene promoter, but its weakness is its poor sensitivity and lack of multiplexing capability. The second approach combines bisulfite-PCR with a DNA microarray to distinguish methylated from unmethylated alleles within the targeted sequences. This approach allows parallel evaluation of the methylation status at numerous CpG sites within many genes of interest. However, it is not sufficiently sensitive to detect minority methylation DNA in a large background of unmethylated DNA. The third approach is methylation-specific PCR (MSP) and its many variations such as MethyLight. This approach is highly sensitive and can detect one methylated allele in 10,000 copies of unmethylated alleles. In addition, real time-based MSP can quantify the abundance of methylated DNA. However, this approach generally analyzes the methylation status one gene at a time and has limited multiplexing capability. In addition, this approach surveys the methylation status only at a few closely neighboring CpG sites. Clearly, these methods either are not sufficiently sensitive, or do not have multiplexing capability, or both.

More recently, two ligation-based approaches have been developed for methylation analysis. In the first approach, a PCR/LDR method is utilized for methylation analysis. This method is similar to the previously noted technology developed for mutation analysis. Briefly, it first utilizes multiplexed PCR to amplify multiple target DNA sequences, followed by ligation reactions. The ligation products are then analyzed using a microarray to determine the methylation status at each target CpG site. In the second approach, a genotyping system is applied to methylation detection. Unlike the first approach, this second approach utilizes ligation to produce both methylated and unmethylated alleles, which is then followed by multiplexed PCR to amplify the sequences containing each target CpG site. The methylation status at each CpG site is analyzed using a microarray. Ligation-based methods can survey the methylation status at numerous CpG sites of many genes of interest. But their detection sensitivity is still relatively poor and thus they are generally used for analysis of the samples containing 10% or more of altered DNA. Such sensitivity is certainly not sufficiently high to detect low abundance methylated DNA in many types of clinical biospecimens, especially in the samples where the abundance of altered DNA can be less than 1%.

Clearly, there is an urgent need in the art for analysis of the methylation status of a large number of CpG sites of many genes of interest in a large background of wild-type DNA in a sensitive and cost-effective manner.

BRIEF DESCRIPTION

The present exemplary embodiment is related to cancer screening by DNA analysis of clinical specimens collected from patients. Specifically, the invention relates to the simultaneous determination of the alteration status of multiple DNA markers in a large background of wild-type DNA.

In a first aspect, the present invention provides a method for surveying the status of multiple mutation markers in a large background of wild-type DNA. The method comprises providing a sample including mutant DNA and wild-type DNA. The mutant DNA includes mutations. The method also comprises amplifying the sample by a first PCR to generate DNA fragments containing the mutation sites. The method also comprises enriching the mutant DNA fragments containing the mutations by performing one or more mutant-specific enrichment cycles to thereby form an enriched system. The method further comprises amplifying the enriched system by a second PCR to generate sufficient amounts of mutant DNA for detection. And, the method comprises surveying the status of the mutation sites in the target DNA sample.

In another aspect, the present invention provides a method for producing sufficiently pure mutant DNA fragments for determining the mutation status at a collection of DNA mutation sites in a large background of wild-type DNA. The method comprises providing a DNA sample including both mutant DNA and wild-type DNA. The method also comprises amplifying DNA sequences including the mutation sites by multiplexed PCR to thereby produce amplicons. And, the method comprises enriching mutant DNA fragments having the mutations from the amplicons of the PCR.

In another aspect, the present invention provides a method for surveying the methylation status of a large number of CpG sites in a large background of unmethylated DNA. The method comprises providing a sample including methylated DNA and unmethylated DNA. The method also comprises treating the sample to convert cytosine groups in the unmethylated DNA to uracil groups, while unaltering the methylated cytosine in the CpG sites. The method further comprises amplifying the treated sample by a first PCR with primers to thereby yield DNA fragments in which all uracil groups are converted to thymine groups. The method also comprises enriching the methylated DNA by performing one or multiple cycles of methylation-specific enrichment to thereby form an enriched system. The method also comprises amplifying the enriched system by a second PCR to generate sufficient amounts of methylated DNA for detection. And, the method comprises surveying the methylation status of the CpG sites.

In yet another aspect, the present invention provides a method for producing sufficiently pure methylated DNA fragments for determining the methylation status at a collection of DNA CpG sites in a large background of unmethylated DNA. The method comprises providing a DNA sample containing both methylated and unmethylated DNA. The method also comprises subjecting the DNA sample to bisulfite treatment. The method further comprises amplifying the treated DNA by multiplexed PCR to thereby produce amplicons. And, the method comprises enriching methylated DNA fragments containing the methylated CpG sites from the amplicons of the PCR.

In yet another aspect, the present invention provides a method for removing primer-primer interaction products produced by multiplexed PCR. The method comprises amplifying target DNA sequences by the multiplexed PCR and purifying the amplified target sequences of the multiplexed PCR by removing primer-primer interaction products by sequence-specific capture.

In yet another aspect, the present invention provides a method for making a multistage multiplex PCR more robust. The method comprises providing a sample containing target sequences. The method also comprises amplifying the sample by a first multiplex PCR to form a first amplified sample containing primer-primer interaction products. The method further comprises removing at least a portion of the primer-primer interaction products. And, the method comprises after the removal of the primer-primer interaction products, forming a second amplified sample by a second PCR.

In another aspect, the present invention provides a method for balancing the yield of a collection of PCR products comprising providing a DNA sample containing the target sequences to be amplified. The method also comprises amplifying the target DNA sequences by a first PCR. The method also comprises balancing the quantity of the target sequences amplified by the first PCR. And, the method comprises amplifying the balanced target DNA sequences by a second PCR.

In yet another aspect, the present invention provides a method for balancing the yield of PCR products produced via a multistage multiplex PCR. The method comprises providing a sample including a first target sequence and a second target sequence. The method also comprises identifying the relative amplification efficiencies of the first target sequence and the second target sequence. And, the method comprises adding to the sample a first probe adapted to target the first target sequence and a second probe adapted to target the second target sequence. The molar ratio of the first probe to the second probe is based upon the relative amplification efficiencies of the first and second target sequences.

DETAILED DESCRIPTION

Figure 1:
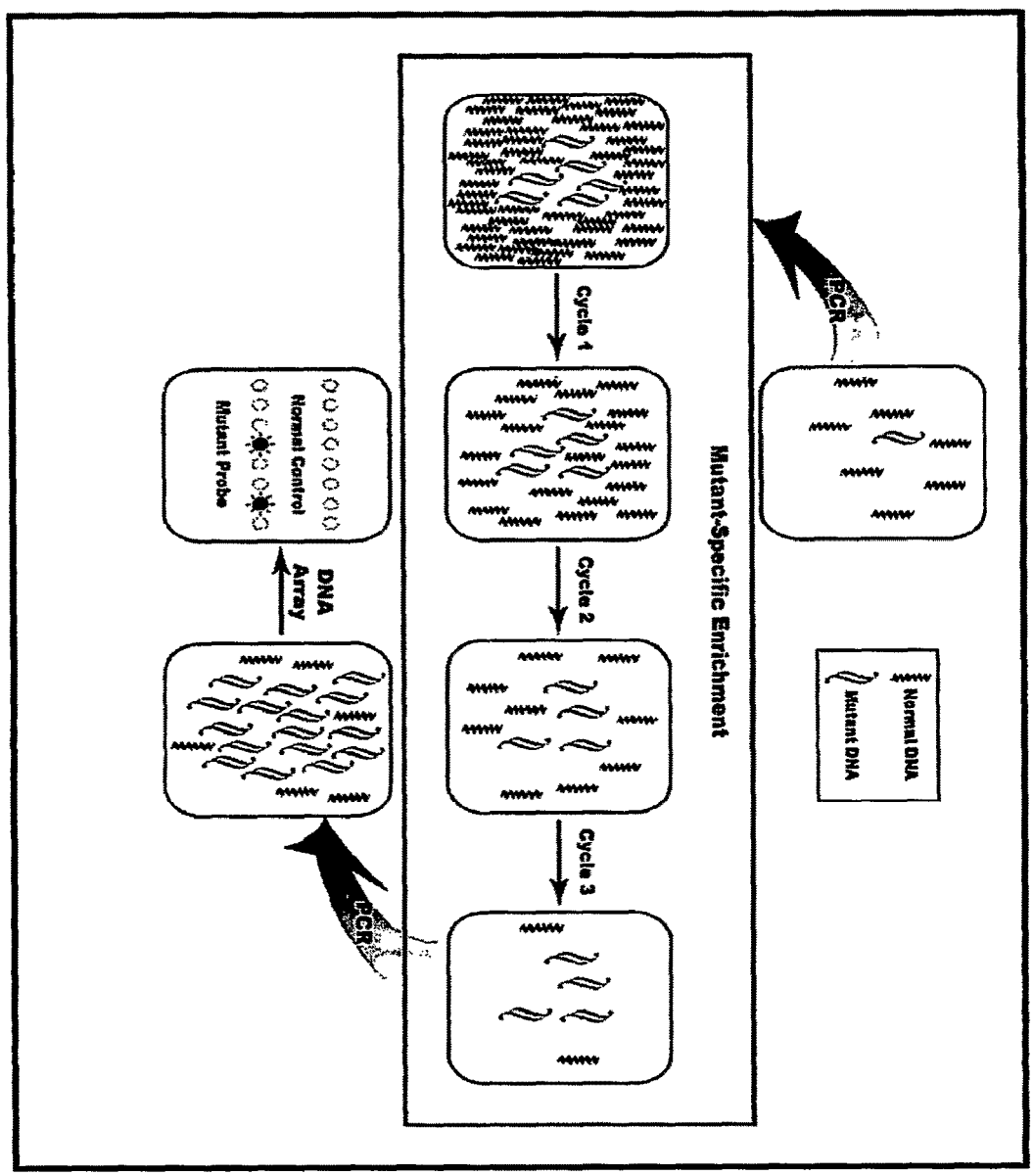
FIG. 1 is a schematic representation illustrating a preferred embodiment method according to the present invention.

The term "wild-type" as used herein refers to a gene which has the characteristics of that gene when isolated from a naturally occurring source. A wild-type gene is that which is most frequently observed in a population and is thus arbitrarily designated as the "normal" or "wild-type" form of the gene. In contrast, the term "modified" or "mutant" refers to a gene which displays modifications in sequence (i.e., altered characteristics) when compared to the wild-type gene.

The term "allele" as used herein refers to two sequences which are different by only one or a few bases.

The term "extension primer" or "primer" refers to a polynucleotide that is complementary to a target sequence. The extension primer is capable of annealing to a target sequence and acting as a primer for polynucleotide synthesis using either the wild-type or mutant polynucleotides or both as templates.

The term "probe" refers to a polynucleotide that is complementary to a target sequence and can preferentially bind to the target sequence.

As used herein, "hybridization" refers to the formation of a complex structure, typically a duplex structure, by nucleic acid strands, e.g. single strands, due to complementary base pairing. Hybridization can occur between exactly complementary nucleic acid strands or between nucleic acid strands that contain minor regions of mismatch. Hybridization conditions should be sufficiently stringent that there is a difference in hybridization intensity between alleles. Hybridization conditions, under which a probe will preferentially hybridize to the exactly complementary target sequence are well known in the art, such as described in Sambrook et al., Molecular Cloning—A Laboratory Manual, Third Edition, Cold Spring Harbor Press, N.Y., 2001, incorporated herein by reference. Stringent conditions are sequence dependent and will be different in different circumstances.

"PCR amplification" or simply "PCR" generally involves the use of a nucleic acid sequence as a template for producing a large number of complements to that sequence. The template may be hybridized to a primer having a sequence complementary to a portion of the template sequence and contacted with a suitable reaction mixture including dNTPs and a polymerase enzyme. The primer is elongated by the polymerase enzyme producing a nucleic acid complementary to the original template. For the amplification of both strands of a double stranded nucleic acid molecule, two primers may be used, each of which may have a sequence which is complementary to a portion of one of the nucleic acid strands. The strands of the nucleic acid molecules are denatured—for example, by heating—and the process is repeated, this time with the newly synthesized strands of the preceding step serving as templates in the subsequent steps. A polymerase chain reaction (PCR) amplification protocol may involve a few to many cycles of denaturation, hybridization and elongation reactions to produce sufficient amounts of the desired nucleic acid.

"Multiplex polymerase chain reaction (PCR)" is a variant of PCR in which two or more sequences or loci are simultaneously amplified in the same reaction.

A "DNA microarray" (also commonly known as DNA chip or DNA array) is a collection of microscopic DNA spots attached to a solid surface, such as glass, plastic or silicon chip forming an array for the purpose of analyzing multiple nucleic acid targets.

Portions of the human genome are referred to as "CpG islands" because those areas are rich in CpG dinucleotides (i.e., cytosine-deoxyribose phosphates followed immediately by a guanine-deoxyribose phosphate) when compared with their surrounding regions. Methylated cytosine in a CpG site remains unaffected by bisulfite treatment, whereas unmethylated cytosines are converted to uracil. Polymerase chain reaction (PCR) can then be used to amplify this DNA such that methylated cytosine is copied to cytosine, and uracil is copied to thymine. Thus, the detection of cytosine in a specific CpG site indicates methylation, whereas the appearance of thymine in a CpG site that normally contains cytosine indicates the presence of unmethylated cytosine in that CpG site. As a result, determining the methylation status at a CpG site can be achieved using a mutation analysis method after subjecting the sample to bisulfite treatment.

The present invention provides a method referred to herein as PEPD (PCR-Enrichment-PCR-Detection) to simultaneously survey the status of a large number of DNA mutation markers in a sensitive and cost-effective manner. FIG. 1 illustrates the principle of PEPD, which generally comprises four major steps. First, a DNA sample containing both mutant and wild-type DNA is amplified by a first multiplex PCR to generate the sufficient quantity of the DNA fragments that contain all the mutation sites targeted for enrichment. Second, mutant DNA is enriched by one or multiple cycles of mutant-specific enrichment. This can be achieved by either depleting wild-type DNA, or selectively capturing mutant DNA, or a combination of both. For example, the PCR products can be hybridized with biotinylated mutant-specific probes to selectively capture the mutant sequences, followed by depleting wild-type sequences. After separation from probes, the enriched DNA can be re-enriched until satisfactory enrichment is achieved. Third, the enriched DNA molecules are then amplified by a second multiplex PCR to generate sufficient amounts of mutant DNA for detection. Fourth, a method such as DNA microarray is used to survey the mutation status of each DNA marker.

There are several aspects contributing to the ability of PEPD to survey the status of hundreds of DNA mutation markers in a vast excess of wild-type DNA.

First, multiple cycles of enrichment can be carried out in PEPD until satisfactory enrichment is achieved, thus making it possible to detect a variety of mutations by a single assay. For example, in order to detect mutant DNA in an excess of normal DNA having a population 1000 times greater than that of the mutant DNA of interest, if one cycle enriches some of the mutant alleles by 1,000 times, while only 10 times for others; then one cycle enrichment would miss some of the mutations. On the contrary, all mutations would be detected by using the same assay if three cycles of enrichment were carried out.

In accordance with a preferred method of PEPD, the number of mutant-specific enrichment techniques or cycles can vary depending upon the particular application and system parameters. However, generally, the number of cycles can range from one to five. Preferably, the number of cycles is one to three.

Second, enrichment is carried out between two rounds of PCR in PEPD. This is a key to the success of PEPD. The quantity of DNA recovered after multiple cycles of enrichment will be low, as stringent conditions are needed to achieve the required enrichment. For example, if the rate of recovering DNA is 1% for each cycle, the overall recovery rate will be 0.0001% after three cycles. Thus, if enrichment is undertaken before PCR, one may not be able to recover even one copy of mutant DNA from clinical samples where the quantity of mutant DNA is low. This is the reason that multiple cycles of enrichment can not be used to directly enrich mutant DNA from original clinical samples. In contrast, after PCR, mutant DNA will be recovered in sufficient quantities. Furthermore, if detection is carried out without the second PCR, there may not be sufficient quantities of mutant DNA remaining for detection after enrichment. In contrast, additional amplification after enrichment will ensure that there are sufficient amounts of mutant DNA for detection. As described next, enrichment between two rounds of PCR also makes amplification and detection of mutant DNA more robust and specific in a multiplexed setting.

Third, cancer screening utilizes a large panel of DNA markers and thus robust multiplexed PCR is essential to multiplexed assaying. Multiplexed PCR strategies, in which two rounds of PCR performed are known. The first-round PCR primers have a target-specific part and universal tail part. The target-specific part allows amplification of a target sequence, while the tail part introduces the sequence for the second PCR which employs primers complementary to the tail parts introduced in the first PCR. PEPD can also use this strategy to amplify multiple sequences. A major problem associated with this strategy is that the second PCR often fails to adequately amplify some of the sequences in this multiplexed setting because of forming primer-primer interaction products during the first PCR. However, in accordance with the present invention, this problem can be minimized in PEPD, since, as a result of enrichment, primer-primer interaction products are also removed, making the second PCR much more robust. In fact, this enrichment approach can be extended to provide a general method to improve amplification of multiplexed PCR.

Figure 2:
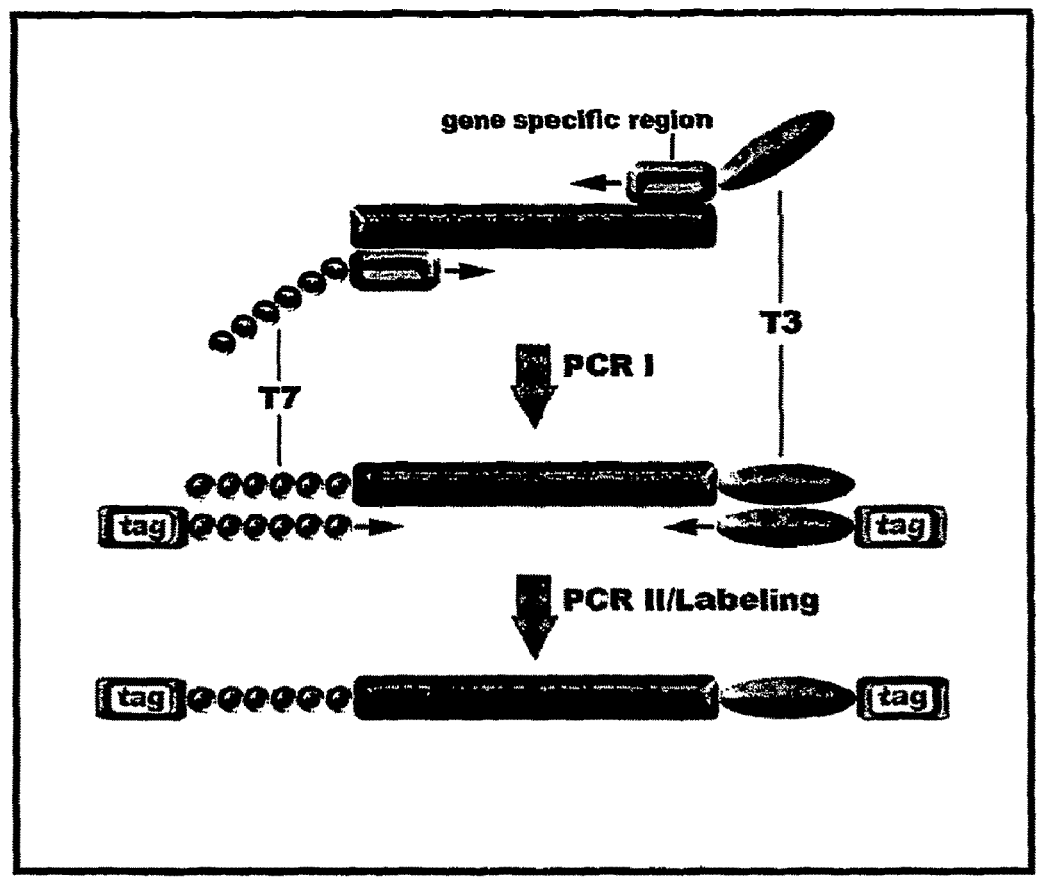
FIG. 2 is a schematic representation illustrating a multiplexed PCR method involving the use of two rounds of PCR.

Fourth, amplification by multiplexed PCR varies from sequence to sequence. That is, some sequences would be poorly amplified in multiplexed PCR. This has been a problem associated with existing methods, as the mutations contained by those poorly amplified sequences could be missed, leading to false-negatives. However, this problem is minimized by PEPD. As shown in FIGS. 1 and 2, mutant DNA can become a majority proportion after enrichment. Amplification by the second PCR depends on the copy number of each sequence. As a consequence, the mutant sequences will be dominant after the second PCR, even when they are poorly amplified in the first PCR. Thus, enrichment ensures adequate amplification of mutant DNA. Because mutation analysis requires the detection of only mutant DNA, PEPD makes the mutation detection much more robust in a multiplexed setting.

The PEPD method is simple, yet powerful and thus can be a universal mutation detection technology platform. Epithelium-derived cancers constitute a majority of all cancers, where specimens such as blood and other bodily fluids can be taken and one can look for mutant DNA to detect cancer. For example, based on the PEPD platform, one can readily develop an assay to survey the status of mutations associated with lung cancer in DNA derived from bronchoalveolar lavage (BAL) for lung cancer screening.

Enrichment in the PEPD strategy can be performed in several different approaches. Enrichment can be performed for example by a mutation-specific hybridization and extraction procedure in which a plurality of mutant-specific probes are contacted with the products of a PCR, i.e. the amplicons which are generally the DNA fragments of interest, under hybridization conditions. Each mutant-specific probe preferentially forms hybrids with a mutant sequence. The mutant-specific probes are preferably attached to a first binding molecule that is capable of binding to a second binding molecule which in turn is preferably attached to a solid support. After hybridization, the hybrids can be captured by the solid support containing the second binding molecule.

Enrichment in the PEPD strategy can also be performed by a competing mutation-specific hybridization and extraction procedure. A collection of mutant-specific probes and normal-competitor probes are contacted or otherwise exposed with the products of a PCR, i.e. the amplicons such as the DNA fragments of interest, under hybridization conditions. Each mutant-specific probe preferentially forms hybrids with a mutant sequence such as contained in a DNA fragment, while the normal competitor probe preferentially forms hybrids with the corresponding wild-type sequence. The mutant-specific probes are further attached to a first binding molecule that is capable of binding to a second binding molecule that is attached to a solid support. After hybridization, the hybrids can be captured by the solid support containing the second binding molecule. Preferably, the molar ratio of each mutant-specific probe to its corresponding normal competitor probe is from about 0.02:1 to about 10:1.

Examples of suitable binding molecules include, but are not limited to biotin, streptavidin, and combinations thereof.

In both the mutation-specific hybridization and extraction enrichment strategy, and the competing mutation-specific hybridization and extraction enrichment strategy, the DNA fragments of interest can be enriched by exaction on a solid support, by releasing the fragments from the solid support and subjecting the system and remaining DNA fragments to additional cycles of enrichment.

The previously noted mutant-specific probes and corresponding normal competitor probes can be any probe suitable for the particular application. Preferred examples of such probes include, but are not limited to oligonucleotides, peptide nucleic acids, locked nucleic acids (LNA), and combinations thereof. LNA is a class of bicyclic nucleic acids where a ribonucleoside is linked between the 2'-oxygen and the 4'-carbon atoms with a methylene unit. Locked Nucleic Acid (LNA) was first described by Wengel and co-workers in 1998 as a novel class of conformationally restricted oligonucleotide analogues.

As noted, in certain applications the first or initial PCR may be a multiplex or multiplexed PCR. In this strategy, two or more pairs of PCR primers are used. Each pair of primers includes a forward primer and a reverse primer. Each pair of primers serves to amplify a sequence containing one or more of the mutation sites. Each primer preferably includes a target-specific part and a universal tail part. The target-specific part flanks or otherwise aligns itself with the sequence of interest to allow for amplification of the sequence. The sequence of the universal tail part is preferably the same for all the forward and the reverse primers. Preferably, the universal tail cannot bind to human genomic sequence. And, preferably, the sequence of the universal tail of the forward primers and the reverse primers can be the same or different.

Furthermore, in procedures employing a second PCR, it is preferred that when the universal tail of the forward and reverse primers of the first PCR are the same, that the second PCR use one universal primer. And, it is preferred that when the universal tail of the forward and reverse primers are different, one universal primer matches the universal tail of the forward primers, and another universal primer matches the universal tail of the reverse primer. Generally, in procedures using a second PCR, the enriched mutant DNA fragments containing the mutations, are contacted or otherwise exposed to universal primers. The universal primers hybridize to the universal tails of the forward and reverse primers to amplify the enriched DNA fragments.

The present invention also provides a method for producing sufficiently pure mutant DNA fragments for determining the mutation status at a plurality of DNA mutation sites in a large background of wild-type DNA. The method comprises providing a DNA sample that includes both mutant and wild-type DNA. The method also comprises amplifying the DNA sequences that contain the mutation sites to thereby produce amplicons. Preferably, this amplifying operation is performed by multiplex PCR. The method also includes enriching the mutant DNA fragments containing the mutations from the amplicons of the PCR. As previously noted, the multiplexed PCR uses two or more pairs of PCR primers in which each pair of the primers hybridize to a sequence containing one or more mutation sites for amplification of the sequence. And, enrichment of the mutant DNA fragments containing the mutations from the amplification products, i.e. amplicons, can be performed by either a mutation-specific hybridization and extraction technique, or a competing mutation-specific hybridization and extraction technique.

Figure 9:
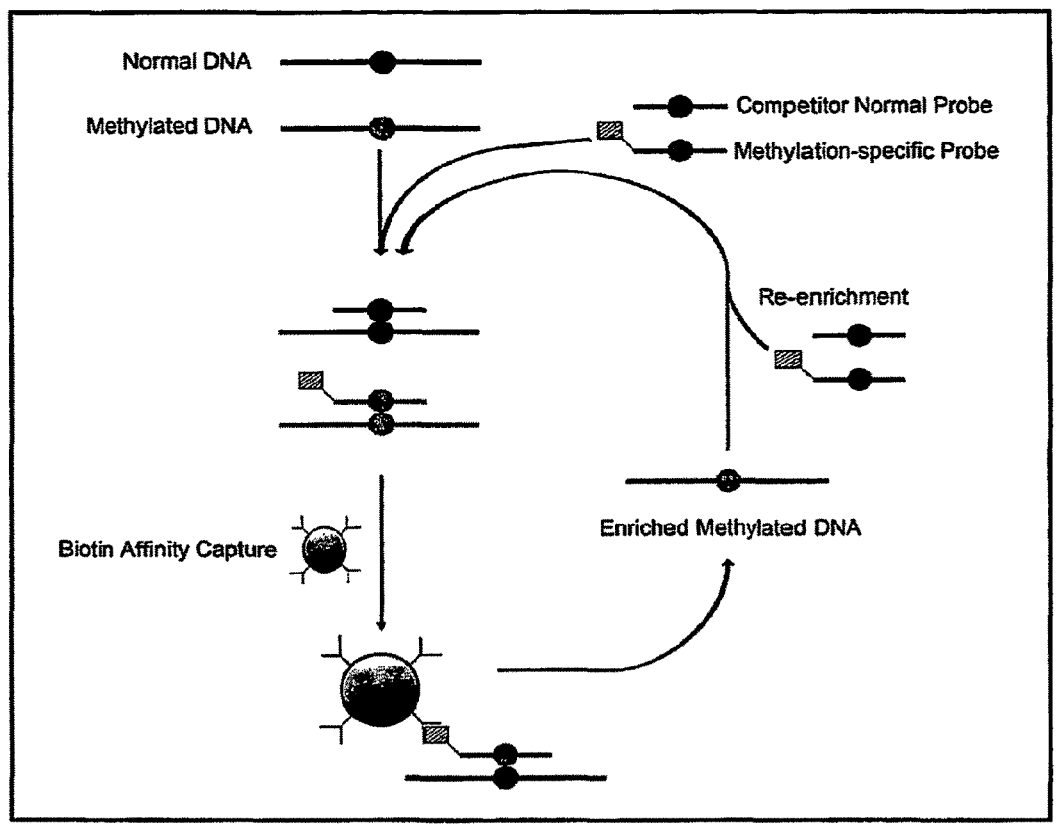
FIG. 9 is a schematic representation of a principle of competitive hybridization strategy used in the MMPA assay.

The present invention also provides a method referred to herein as MMPA (Multiplexed Methylation Profiling Assay) for methylation analysis. Specifically, this method allows the use of a single assay to simultaneously determine the methylation status at numerous CpG sites in a very large background of unmethylated DNA. FIG. 9 displays the principle of MMPA, which generally comprises five steps. First, a sample containing both methylated and unmethylated DNA is treated using a bisulfite reaction which converts cytosine to uracil whereas the methylated cytosine residues are resistant to this conversion. Second, the treated DNA is amplified by a first PCR with specific primers to yield fragments, in which all uracil residues are converted to thymine, whereas methylated cytosine in CpG sites residues are unaltered. This PCR will generate the sufficient quantity of DNA for enrichment. Third, methylated DNA is enriched using one or multiple cycles of methylation-specific enrichment techniques. Examples of such techniques include depleting unmethylated DNA, selectively capturing methylated DNA, or a combination of these. Fourth, the enriched DNA molecules are then amplified by a second PCR to generate sufficient amounts of DNA for detection. And fifth, the methylation status at each target CpG site is then surveyed.

Several aspects are associated with MMPA, thereby making it possible to simultaneously study the methylation status at numerous CpG sites in a vast excess of unmethylated DNA.

First, MMPA utilizes competitive hybridization to improve the specificity of hybridization, where DNA fragments produced by the first round PCR hybridize with both methylation-specific probes directed to the chosen methylated alleles and competitor probes complementary to the corresponding unmethylated alleles. Because the methylation-specific probes are biotinylated, while the competitor probes are not, only methylation-specific probe/target hybrids can be captured, such as by streptavidin-coated beads. The captured hybrid is then eluted, yielding single-stranded target enriched for methylated alleles. The enriched DNA can be enriched again until all methylated alleles are more abundant than the corresponding unmethylated alleles. FIG. 9 illustrates the principle of competitive hybridization used in the MMPA embodiment.

Second, the hybridization specificity can vary greatly with sequences, leading to a large variation in enrichment. However, hybridization is a physical process and therefore does not artificially create methylated DNA. Hence, multiple cycles of hybridization is used in MMPA to enable satisfactory enrichment of every target sequence. For example, in order to detect methylation in an excess of unmethylated DNA having a population 1,000 times greater than that of the methylated species of interest, and where one cycle of hybridization enriches some sequences by 1,000 times, while only 20 times for others; three cycles of hybridization can be used to ensure that all methylated alleles are adequately enriched. This is the reason that one assay can simultaneously reveal the methylation status at numerous CpG sites in a large background of unmethylated DNA.

In accordance with the preferred method of MMPA, the number of methylation-specific enrichment techniques or cycles can vary depending upon the particular application and system parameters. However, generally, the number of cycles can range from one to five. Preferably, the number of cycles is one to three.

Third, methylation-specific enrichment is carried out between two rounds of PCR in MMPA. This is a key to the success of MMPA. The DNA quantity recovered after multiple cycles of hybridization will be very low as stringent hybridization and washing conditions are used for enrichment. For example, if the DNA recovery rate is 1% for one cycle, the overall recovery rate will be only 0.0001% after three cycles. Thus, if enrichment is undertaken prior to PCR, it may not be possible to recover even one copy of methylated DNA from biospecimens where the quantity of methylated DNA is low. PCR prior to enrichment can produce sufficient amounts of methylated DNA for enrichment. Moreover, if detection is carried out without additional amplification after enrichment, there may not be sufficient quantities of methylated DNA left for detection. Hence, amplification after enrichment ensures that there are sufficient amounts of methylated DNA for detection. As described below, enrichment between two rounds of PCR also makes amplification and detection of methylated DNA more robust and specific in a multiplexed setting.

Fourth, a two-round PCR strategy is preferably used in MMPA. The first PCR primers have both a target-specific part and universal tail part. The target-specific part allows amplification of a target sequence, while the tail part introduces the universal sequences for the second PCR which employs two primers complementary to the tail parts introduced by the first PCR. One of the problems associated with two-round PCR strategies is that the second round PCR can often fail to adequately amplify some of the sequences in this multiplexed setting due to the formation of primer-primer interaction products during the first round PCR. However, this problem is significantly minimized by MMPA. This is because, as a result of enrichment, primer-primer interaction products are removed, making the second round PCR more robust. In fact, this approach can be a universal method to improve high-order multiplexed PCR.

Fifth, another problem of multiplexed PCR is that the PCR amplification efficiency can vary with sequences. This can be a problem especially for methylation analysis, as the poorly amplified methylated sequences may not be detectable. However, this problem can also be significantly minimized in MMPA, as methylation-specific enrichment makes methylated DNA more abundant than unmethylated DNA after enrichment. Because amplification by the second PCR depends mainly on the copy number of each sequence, the methylated sequences will become a majority of the population after the second round PCR, even when they are poorly amplified by the first round PCR. Additionally, a probe extraction process can balance the yield of the PCR products amplified by multiplexed PCR. This is achieved by optimizing the molar ratio of the hybridization probes so that poorly amplified sequences can be more effectively captured, while better amplified sequences are captured less efficiently during the course of hybridization. For example, if amplification of Sequence A by the first PCR is more efficient than that of Sequence B, lesser amounts of the probe targeting Sequence A will be used to capture Sequence A and thus the quantity of both Sequences A and B recovered after enrichment can be balanced, making it possible to detect both sequences.

MMPA offers several advantages over existing methylation analysis methods. First, one MMPA assay can reveal the methylation status at numerous CpG sites of many genes of interest, thereby allowing an analysis using minimal amounts of starting materials. Second, MMPA greatly improves the detection sensitivity while retaining its high-order multiplexing capability. In accordance with the present invention, it has been demonstrated that MMPA can detect one methylated allele in an excess of unmethylated alleles having a population 10,000 times greater than that of the methylated allele. This sensitivity is, in fact, comparable to the sensitivity of methylation specific PCR (MSP) which is the most sensitive method, but has limited multiplexing capability. Third, enrichment in MMPA is achieved by hybridization that, unlike PCR and ligation, is a physical process and does not artificially create methylated DNA, thereby making MMPA highly specific. In contrast, greater sensitivity could be achieved at the cost of increasing false positives with an amplification method. Fourth, MMPA is cost-effective as one assay can simultaneously reveal the methylation status at numerous CpG sites of many genes of interest. And fifth, the enrichment procedure used in MMPA is simple and three cycles of hybridization can be completed in relatively short time periods. In addition, sample preparation in MMPA can be carried out using a liquid-handling system and thus the MMPA assay can be a high-throughput process and amenable to automation.

Enrichment in the MMPA strategy can be performed by several different approaches. Enrichment can be performed for example by a methylation-specific hybridization and extraction procedure in which a plurality of methylation-specific probes are contacted with the products of a PCR, i.e. the amplicons which are generally the DNA fragments of interest, under hybridization conditions. Each methylation-specific probe preferentially forms hybrids with a methylated sequence. The methylation-specific probes are preferably attached to a first binding molecule that is capable of binding to a second binding molecule which in turn is preferably attached to a solid support. After hybridization, the hybrids can be captured by the solid support containing the second binding molecule.

Enrichment in the MMPA strategy can also be performed by a competing methylation-specific hybridization and extraction procedure. A collection of methylation-specific probes and unmethylated-competitor probes are contacted or otherwise exposed with the products of a PCR, i.e. the amplicons such as the DNA fragments of interest, under hybridization conditions. Each methylation-specific hybridization probe preferentially forms hybrids with a methylated sequence such as contained in a DNA fragment, while the unmethylated competitor probe preferentially forms hybrids with the corresponding unmethylated sequence. The methylation-specific hybridization probes are further attached to a first binding molecule that is capable of binding to a second binding molecule that is attached to a solid support. After hybridization, the hybrids can be captured by the solid support containing the second binding molecule. Preferably, the molar ratio of each methylated-specific probe to its corresponding unmethylated competitor probe is from about 0.02:1 to about 10:1.

Examples of suitable binding molecules include, but are not limited to biotin, streptavidin, and combinations thereof.

In both the methylation-specific hybridization and extraction enrichment strategy, and the competing methylation-specific hybridization and extraction enrichment strategy, the DNA fragments of interest can be enriched by extraction on a solid support, by releasing the fragments from the solid support and subjecting the system and remaining DNA fragments to additional cycles of enrichment.

The previously noted methylation-specific probes and corresponding unmethylated competitor probes can be any probe suitable for the particular application. Preferred examples of such probes include, but are not limited to oligonucleotides, peptide nucleic acids, locked nucleic acids, and combinations thereof.

As noted, in certain applications the first or initial PCR may be a multiplex or multiplexed PCR. In this strategy, two or more pairs of PCR primers are used. Each pair of primers includes a forward primer and a reverse primer. Each pair of primers serves to amplify a sequence containing one or more of the methylation sites. Each primer preferably includes a target-specific part and a universal tail part. The target-specific part flanks or otherwise aligns itself with the sequence of interest to allow for amplification of the sequence. The sequence of the universal tail part is preferably the same for all the forward and the reverse primers. Preferably, the universal tail cannot bind to human genomic sequence. And, preferably, the sequence of the universal tail of the forward primers and the reverse primers can be the same or different.

Furthermore, in procedures employing a second PCR, it is preferred that when the universal tail of the forward and reverse primers of the first PCR are the same, that the second PCR use one universal primer. And, it is preferred that when the universal tail of the forward and reverse primers are different, one universal primer matches the universal tail of the forward primers, and another universal primer matches the universal tail of the reverse primer. Generally, in procedures using a second PCR, the enriched DNA fragments containing the methylation sites, are contacted or otherwise exposed to universal primers. The universal primers hybridize to the universal tails of the forward and reverse primers to amplify the enriched DNA fragments.

The present invention also provides a method for producing sufficiently pure methylated DNA fragments for determining the methylation status at a plurality of DNA CpG sites in a large background of unmethylated DNA. The method comprises providing a DNA sample that includes both methylated and unmethylated DNA. The method also comprises amplifying the DNA sequences that contain the methylation sites to thereby produce amplicons. Preferably, this amplifying operation is performed by multiplex PCR. The method also includes enriching the methylated DNA fragments containing the methylated CpG sites from the amplicons of the PCR. As previously noted, the multiplexed PCR uses two or more pairs of PCR primers in which each pair of the primers hybridize to a sequence containing one or more of the methylation sites for amplification of the sequence. And, enrichment of the methylated DNA fragments containing the methylations from the amplification products, i.e. amplicons, can be performed by either a methylated-specific hybridization and extraction technique or a competing methylation-specific hybridization and extraction technique.

All of the foregoing methods are particularly directed to samples obtained from clinical biospecimens collected from patients, including human tumor tissues, peripheral blood, stool, urine, bodily fluids, washing fluids associated with medical procedures, and combinations thereof. The samples or rather DNA samples of suspected biospecimens typically contain DNA alteration sites that can be in the form of one or more single base substitutions, one or more single base insertions, one or more single base deletions, methylation at one or more CpG sites, and combinations thereof. Typical molar ratios of wild-type DNA to altered DNA in such samples can range from about 2:1 to about 100,000:1.

As previously noted, the present invention also provides a method for removing primer-primer interaction products produced by a multiplex PCR. Generally, the method comprises amplifying target DNA sequences by the multiplex PCR and then purifying the amplified target sequences of the multiplex PCR by removing the primer-primer interaction products by a sequence-specific capture. As will be appreciated, the multiplex PCR uses two or more pairs of PCR primers in which each pair of primers is adapted to amplify a particular target sequence.

Sequence-specific capture is preferably performed by contacting or otherwise exposing, a plurality of sequence-specific probes with the products or amplicons of the multiplex PCR under hybridization conditions. Each sequence-specific probe preferentially forms hybrids with a target sequence. The sequence-specific probes are further attached to a first binding molecule that is capable of binding to a second binding molecule that is attached to a solid support. After hybridization, the hybrids can be captured by the solid support containing the second binding molecule. The sequence-specific capture approach can be repeated such that DNA fragments extracted by the solid support are released from the solid support and further subjected to additional cycles of the sequence-specific capture. The various binding molecules are as previously described and can include biotin, streptavidin, and combinations thereof.

A wide array of probes can be used for sequence-specific capture methods. Non-limiting examples include oligonucleotides, peptide nucleic acids, locked nucleic acids, and combinations thereof. Preferably, the sequence-specific probes do not bind to the sequences of the primers used in the multiplex PCR.

The present invention can also be applied to render a multistage multiplex PCR more robust. The method involves providing a sample that contains a target sequence, and then amplifying the sample by a first multiplex PCR to form a first amplified sample containing primer-primer interaction products. Next, at least a portion of the primer-primer interaction products are removed. Then, a second multiplex PCR can be used to form a second amplified sample.

The invention also provides a method for balancing the yield of a plurality of PCR products. The method comprises providing a DNA sample containing the target sequences to be amplified. The method involves then amplifying the target sequences by a first PCR. The quantity of the target sequences can then be balanced or otherwise adjusted. And, the balanced target sequences are then amplified by a second PCR. In this approach, the first PCR is preferably multiplexed PCR using two or more pairs of PCR primers. Each pair of primers includes a forward primer and a reverse primer. Each pair of primers is adapted to amplify the target sequence of interest. Each primer includes both a target-specific part and a universal tail part. The target-specific part flanks the target sequence to allow for amplification of the sequence and the sequence of the universal tail part is the same for all forward and reverse primers. Preferably, the universal tail cannot bind to any DNA sequences in the sample. And, preferably, the sequence of the universal tail of the forward and reverse primers can be the same or different.

The quantity of the target sequences amplified by the first PCR is preferably balanced by sequence-specific capture. A plurality of sequence-specific probes are contacted with amplicons of the first PCR under hybridization conditions in which each sequence-specific probe preferentially forms hybrids with a target sequence. The sequence-specific probes are further attached to a first binding molecule that is capable of binding to a second binding molecule that is attached to a solid support. After hybridization, the hybrids are captured by the solid support containing the second binding molecule. Preferably the molar ratio of the sequence-specific probes is optimized so that the poorly amplified sequences can be more effectively captured by adding larger quantities of the sequence-specific probes corresponding to the poorly amplified sequences, and better amplified sequences are captured less efficiently during the course of hybridization by adding less quantities of the sequence-specific probes corresponding to the better amplified sequences.

The sequence-specific probes can be nearly any type of probe, such as oligonucleotides, peptide nucleic acids, locked nucleic acids, and combinations thereof.

In the noted balancing strategy using sequence-specific capture, the first binding molecule can be, for example biotin, streptavidin, and combinations thereof, and the second binding molecule can be selected from the group consisting of streptavidin, biotin, and combinations thereof.

The sequence specific capture can be repeated, wherein the DNA fragments extracted by the solid support are released from the solid support and further subjected to additional cycles of the sequence-specific capture to achieve the best balancing of the quantities of the target-sequences.

The present invention also provides a method for balancing the yield of PCR products produced by a multistage multiplex PCR strategy. The method comprises providing a sample including a first target sequence and a second target sequence. Next, the method involves identifying the relative amplification efficiencies of the first target sequence and the second target sequence. And, the method includes adding to the sample a first probe adapted to target the first target sequence and a second probe adapted to target the second target sequence. The molar ratio of the first probe to the second probe is based upon the relative amplification efficiencies of the first and second target sequences. If the first target sequence has a higher amplification efficiency than the second target sequence, then the molar ratio of the first probe to the second probe is increased.

EXAMPLES

The following examples contained herein are intended to illustrate but not limit the invention.

Example 1

This example is to demonstrate the use of competing mutation-specific hybridization and extraction to improve the specificity of enrichment. In this method, two oligo probes were used for each mutation site, one of which (mutant probe) is complementary to mutant DNA, another of which (normal competitor probe) is complementary to wild-type DNA. However, only the mutant probes are biotinylated and thus only they and the mutant DNA carried by them can be captured, enriching mutant DNA. The use of two oligo probes is based on the consideration that the $T_m$ change of oligos may not be sufficiently large to discriminate two alleles differing by one base and that adding a normal competitor probe can create a competition in hybridization, improving enrichment.

In this example, we detected a G→T mutation in the first base of codon 12 of K-ras. Wild-type DNA was obtained from Promega (Madison, Wis.). Mutant DNA was extracted from the BAL samples of the patients with lung cancer. The samples containing low-abundant mutant DNA were created by diluting mutant DNA with wild-type DNA. The abundance and the quantity of mutant DNA in the created samples were estimated based on the copy number of mutant DNA in the original samples and amounts of wild-type DNA added. In this example, the sample containing 1% of mutant DNA (0.05 ng of mutant DNA in 5 ng of normal DNA) was used studied.

First PCR: The DNA sample was first subjected to the first PCR where the forward and reverse PCR primers have a tail of either T7 or T3 and their sequences were: 5'-GTAATAC-GACTCACTATAGGAGGCCTGCTGAAAATGACTG-3' (SEQ ID NO: 1) and 5'-AATTAACCCTCACTAAAGGGT-TGGATCATATTCGTCCACAA-3' (SEQ ID NO: 2), respectively. 10 pmol of each forward and reverse primer, 0.2 mM of each dNTPs, 1×PCR buffer with 2 mM of $MgCl_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Competing Mutation-specific hybridization and extraction: The products of the first PCR were incubated with a mixture of the mutant and normal competitor probes for competing mutation-specific enrichment. 2 µL of the PCR product amplified above, 1×PCR buffer, 5 mM of EDTA, and the mutant and normal competitor probes were added to the reaction tube in a total volume of 20 uL. The sequences of the mutant and normal competitor probes were: 5'-biotin-TTG-GAGCTTGTGGCGTAG-3' (SEQ ID NO: 3) and 5'-TTG-GAGCTGGTGGCGTAG-3' (SEQ ID NO: 4), respectively. The molar ratio of the normal competitor to mutant probes was varied to determine the effect of this ratio on enrichment. Hybridization of the probes with the PCR products was carried out by first denaturing DNA at 95° C. for 5 min, followed by slowly ramping down the temperature to 25° C. at 0.04° C./sec. After hybridization, 5 µL of streptavidin-coated magnetic beads (Dynal Biotech, Oslo, Norway) in 20 µl 2× B&W buffer were added to the hybridization tube which was further incubated for 45 min at room temperature. The beads were washed 3 times by 180 µL of 1×TE buffer. Thereafter, 5 µL of 1×TE buffer was then added to resuspend the beads. The beads were heated at 95° C. for 5 min, followed by transferring the supernatant to a clean tube.

Second PCR: About 1 uL of the enriched DNA was used as templates for the second PCR amplification which utilized T7 of 5'-GTAATACGACTCACTATAGG-3' (SEQ ID NO: 5) and T3 of 5'-AATTAACCCTCACTAAAGGG-3' (SEQ ID NO: 6) as the forward and reverse primers, respectively. 10 pmol of forward and reverse primer, 0.2 mM of each dNTPs, 1×PCR buffer, 2 mM of MgCl2, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Mutation Analysis: The degree of enrichment was examined by a MALDI-TOF-based mini-sequencing assay. The products of the second PCR were first treated with Phosphatase (USB, Cleveland, Ohio) and DNA exonecularse I (USB, Cleveland, Ohio) for 30 min at 37° C., followed by 10 min at 80° C. 2.5 µL of the treated PCR products was mixed with 2.5 µL mixture of 0.025 mM of each ddATP, ddGTP and ddTTP, 0.1 mM of dCTP, 2× ThermoSequenase buffer containing 1.5 mM $MgCl_2$, 1 pmol/µL of mini-sequencing primer, 0.2 u/µL of ThermoSequenase. Mini-sequencing was conducted under the condition of 2 min at 94° C. for preheat, followed by 60 cycles of 20 sec at 94° C., 20 sec at 50° C., 20 sec at 72° C. The mini-sequencing extension primer was: 5'-CAAGGCACTCTTGCCTACGCCAC-3' (SEQ ID NO: 7). 10 µL of $NH_4OH$ treated ion exchange beads were incubated with the mini-sequencing products for desalting. The MALDI sample was prepared by mixing the extension products with the 3-HPA matrix. The sample was dried and then analyzed by MALDI-TOF. The degree of enrichment was determined by comparing the intensity of the peaks corresponding to the mutant and normal alleles.

Figure 3:
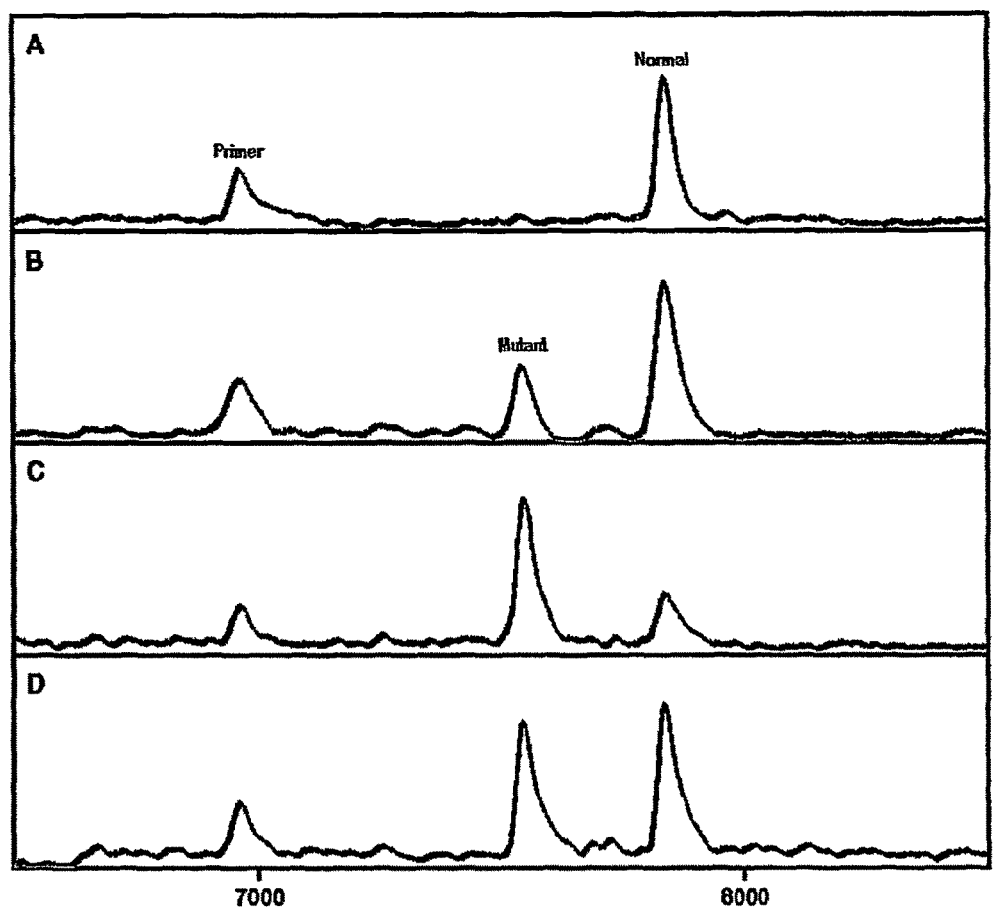
FIG. 3 illustrates the results of enriching a sequence containing a G→T mutation at the first base of codon 12 of k-ras with different ratios of normal competitor and mutant probes, (A) no normal competitor probe; (B) 2.5 times more excess; (C) 7.5 times more excess; and (D) 15 times more excess of the normal competitor probe. The sample contains 1% of mutant DNA and was enriched once. The mutant probe was fixed at 2.5 pmole.

FIG. 3 displays enrichment of a sequence containing a G→T mutation at the first base of codon 12 of K-ras at different ratios of the normal competitor probe to mutant probe. The peaks labeled by Primer, Mutant, and Normal in FIG. 3 correspond to the primer, the extension products of mutant and normal sequences, respectively. The tested sample was enriched once. It was seen that no peak corresponding to mutant DNA was seen in the absence of the normal competitor probes (FIG. 3A). However, the mutant peak appeared after adding 2.5, or 7.5, or 15 folds more excess of the normal probe (FIG. 3B to 3D), demonstrating the dramatic improvement of enrichment after adding the normal competitor probes.

Example 2

This example demonstrates the effect of the quantity of the probes used on enrichment.

In this example, we detected a G→T mutation in the first base of codon 12 of K-ras. Wild-type DNA was obtained from Promega (Madison, Wis.). Mutant DNA was extracted from the BAL samples of the patients with lung cancer. The samples containing low-abundant mutant DNA were created by diluting mutant DNA with wild-type DNA. The abundance and the quantity of mutant DNA in the created samples were estimated based on the copy number of mutant DNA in the original samples and amounts of wild-type DNA added. In this example, the sample containing 1% of mutant DNA (0.05 ng of mutant DNA in 5 ng of normal DNA) was used studied.

First PCR: The DNA sample was first subjected to the first PCR where forward and reverse PCR primers have a tail of either T7 or T3 and the sequences of the forward primer were: 5'-GTAATACGACTCACTATAGGAGGCCT-GCTGAAAATGACTG-3' (SEQ ID NO: 1) and the sequence of the reverse primer was 5'-AATTAACCCTCAC-TAAAGGGTTGGATCATATTCGTCCACAA-3' (SEQ ID NO: 2). 10 pmol of each forward and reverse primer, 0.2 mM of each dNTPs, 1×PCR buffer with 2 mM of $MgCl_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Competing mutation-specific hybridization and extraction: The products of the first PCR were incubated with a mixture of the mutant and normal competitor probes for competition mutation-specific enrichment. 2 µL of the PCR product amplified above, 1×PCR buffer, 5 mM of EDTA, and the mutant and normal competitor probes were added to a reaction tube in a total volume of 20 uL. The molar ratio of the normal competitor probe to mutant probes was fixed at 7.5, and the quantity of the mutant probes ranged from 0.1 to 1 pmoles. The sequences of the mutant and normal competitor probes were: 5'-biotin-TTGGAGCTTGTGGCGTAG-3' (SEQ ID NO: 3) and 5'-TTGGAGCTGGTGGCGTAG-3' (SEQ ID NO: 4), respectively. Hybridization of the probes with the PCR products was carried out by first denaturing DNA at 95° C. for 5 min, followed by slowly ramping down the temperature to 25° C. at 0.04° C./sec. After hybridization, 5 µL of streptavidin-coated magnetic beads (Dynal Biotech, Oslo, Norway) in 20 µl 2× B&W buffer were added to the hybridization tube which was further incubated for 45 min at room temperature. The beads were washed 3 times by 180 µL of 1×TE buffer. Thereafter, 5 µL of 1×TE buffer was then added to resuspend the beads. The beads were heated at 95° C. for 5 min, followed by transferring the supernatant to a clean tube.

Second PCR: About 1 µL of the enriched DNA was used as templates for the second PCR amplification which utilized T7 of 5'-GTAATACGACTCACTATAGG-3' (SEQ ID NO: 5) and T3 of 5'-AATTAACCCTCACTAAAGGG-3' (SEQ ID NO: 6) as the forward and reverse primers, respectively. 10 pmol of forward and reverse primer, 0.2 mM of each dNTPs, 1×PCR buffer 2 mM of MgCl$_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Mutation Analysis: The degree of enrichment was examined by a MALDI-TOF-based mini-sequencing assay. The products of the second PCR were first treated with Phosphatase and DNA exonecularse I for 30 min at 37° C., followed by 10 min at 80° C. 2.5 µL of the treated PCR products was mixed with 2.5 µL mixture of 0.025 mM of each ddATP, ddGTP and ddTTP, 0.1 mM of dCTP, 2× ThermoSequenase buffer containing 1.5 mM MgCl$_2$, 1 pmol/µL of mini-sequencing primer, 0.2 u/µL of ThermoSequenase. Mini-sequencing was conducted under the condition of 2 min at 94° C. for preheat, followed by 60 cycles of 20 sec at 94° C., 20 sec at 50° C., 20 sec at 72° C. The mini-sequencing extension primer was: 5'-CAAGGCACTCTTGCCTACGCCA-3' (SEQ ID NO: 7). 10 µL of NH$_4$OH treated ion exchange beads were incubated with the mini-sequencing products for desalting. The MALDI sample was prepared by mixing the extension products with the 3-HPA matrix. The sample was dried and then analyzed by MALDI-TOF. The degree of enrichment was determined by comparing the intensity of the peaks corresponding to the mutant and normal alleles.

Figure 4:
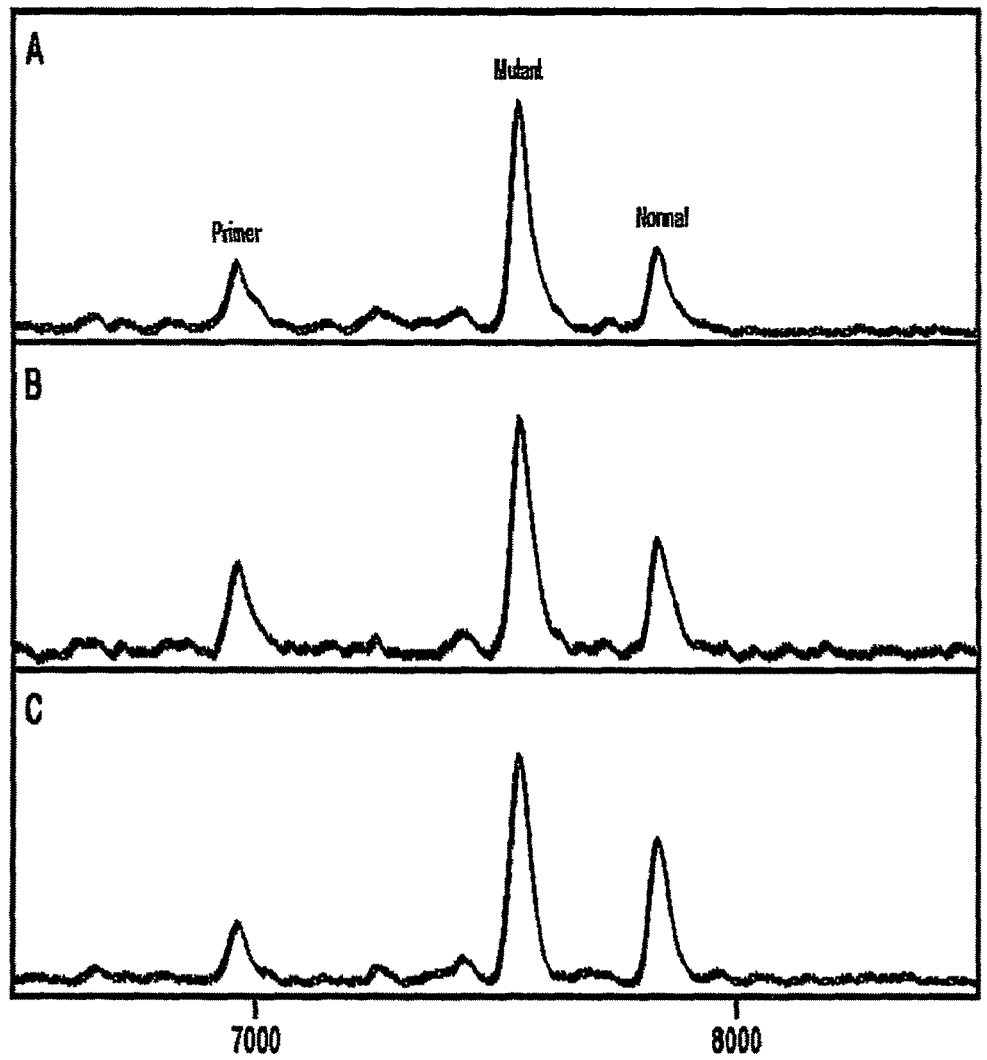
FIG. 4 illustrates the results of enriching a sequence containing a G→T mutation at the first base of codon 12 of k-ras using (A) 1 pmole; (B) 0.2 pmole; and (C) 0.1 pmole of the mutant probe. The sample contained 1% of mutant DNA and was enriched only once. The ratio of the normal to mutant probe was fixed at 7.5.

FIG. 4 displays enrichment of a sequence containing a G→T mutation at the first base of codon 12 of k-ras with different amounts of the mutant probes. The sample contained 1% of mutant DNA and was enriched once. It was found that similar enrichment was achieved when the quantity of the mutant probes ranged from 0.1 to 1 pmoles.

Example 3

This example is to demonstrate the improvement of enrichment using multiple cycles of hybridization and extraction. In this example, we used a sequence containing a C→T mutation on the first base of codon 1450 of APC. Wild-type DNA was obtained from Promega (Madison, Wis.). Mutant DNA was extracted from a colon cancer cell line. The samples containing low-abundant mutant DNA were created by diluting mutant DNA with wild-type DNA. The abundance and the quantity of mutant DNA in the created samples were estimated based on the copy number of mutant DNA in the original samples and amounts of wild-type DNA added. In this example, the samples containing 1%, or 0.1%, or 0.01% of mutant DNA were studied, respectively.

The forward and reverse primer of the first PCR has a tail of either T7 or T3 and their sequences were: 5'-GTAATAC-GACTCACTATAGGCTTCCAGATAGCCCTGGACA-3' (SEQ ID NO: 8) and 5'-AATTAACCCTCAC-TAAAGGGGCAGCATTTACTGCAGCTTG-3' (SEQ ID NO: 9), respectively. The mini-sequencing extension primer was: 5'-CCTCAAACAGCTCAAACCAAG-3' (SEQ ID NO: 10). The mutant probe and the normal competitor probe were: 5'-biotin-TCAAACCAAGTGAGAAGTA (SEQ ID NO: 11) and 5'-TCAAACCAAGCGAGAAGTA-3' (SEQ ID NO: 12), respectively.

First PCR: 10 pmol of each forward and reverse primer, 0.2 mM of each dNTPs, 1×PCR buffer, 2 mM of MgCl$_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Enrichment: The products of the first PCR were incubated with a mixture of the mutant and normal probes for competing mutation-specific hybridization and extraction. In a total volume of 20 uL, containing 2 µL of the PCR product amplified above, 1×PCR buffer, 5 mM of EDTA, and 0.01 pmol/µL of the mutant and 0.075 pmol/µL normal competitor probes were added to the tube. The molar ratio of the normal competitor probe to mutant probe was 7.5. Hybridization of the probes with the PCR products was carried out by first denaturing DNA at 95° C. for 5 min, followed by slowly ramping down the temperature to 25° C. at 0.04° C./sec. After hybridization, 5 µL of streptavidin-coated magnetic beads (Dynal Biotech; Oslo, Norway) in 20 µl 2× B&W buffer were added to the hybridization tube which was further incubated for 45 min at room temperature. The beads were washed 3 times by 180 µL of 1× TE buffer. Thereafter, 5 µL of 1×TE buffer was then added to resuspend the beads. The beads were heated at 95° C. for 5 min, followed by transferring the supernatant to a clean tube.

Second PCR: About 1 µL of the enriched DNA was used as templates for the second PCR amplification which utilized T7 of 5'-GTAATACGACTCACTATAGG-3' (SEQ ID NO: 5) and T3 of 5'-AATTAACCCTCACTAAAGGG-3' (SEQ ID NO: 6) as the forward and reverse primers, respectively. 10 pmol of forward and reverse primer, 0.2 mM of each dNTPs, 1×PCR buffer, 2 mM of MgCl$_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Mutation Analysis: The degree of enrichment was examined by a MALDI-TOF-based mini-sequencing assay. The products of the second PCR were first treated with Phosphatase and DNA exonecularse I for 30 min at 37° C., followed by 10 min at 80° C. 2.5 µL of the treated PCR products was mixed with 2.5 µL mixture of 0.025 mM of each ddATP, ddGTP and ddTTP, 0.1 mM of dCTP, 2× ThermoSequenase buffer containing 1.5 mM MgCl$_2$, 1 pmol/µL of mini-sequencing primer, 0.2 u/µL of ThermoSequenase. Mini-sequencing was conducted under the condition of 2 min at 94° C. for preheat, followed by 60 cycles of 20 sec at 94° C., 20 sec at 50° C., 20 sec at 72° C. 10 µL of NH$_4$OH treated ion exchange beads were incubated with the mini-sequencing products for desalting. The MALDI sample was prepared by mixing the extension products with the 3-HPA matrix. The sample was dried and then analyzed by MALDI-TOF. The degree of enrichment was determined by comparing the intensity of the peaks corresponding to the mutant and normal alleles.

Figure 5:
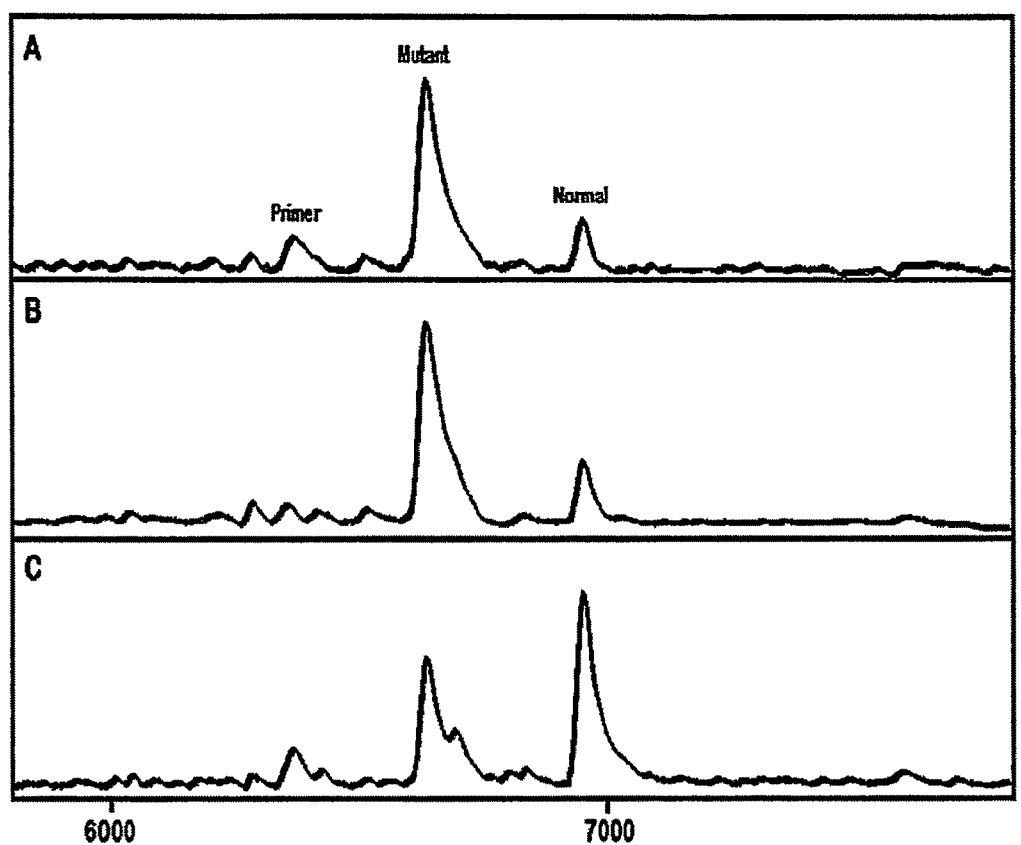
FIG. 5 illustrates the results of enriching a sequence containing a C→T mutation at the first base of codon 1450 of APC using one (A), two (B), and three (C) cycles of enrichment, respectively. The samples contained 1% (A), 0.1 (B), and 0.01% (C) of mutant DNA, respectively.

FIG. 5 shows enrichment of a sequence containing a C→T mutation at the first base of codon 1450 of APC using one (5A), two (5B), and three (5C) cycles of enrichment, where the samples contained 1% (5A), 0.1% (5B) and 0.01% (5C) of mutant DNA, respectively. Clearly, the peak of the mutant DNA in FIG. 5C is comparable to the peak of wide-type DNA, suggesting a successful enrichment of this sequence by about 10,000 folds with three cycles of enrichment.

Example 4

This example demonstrates the effect of the DNA size on enrichment. In this example, we studied three sequences of different size, all of which contains a C→T mutation on the first base of codon 1450 of APC. The first sequence is 158 bp long in length, the second sequence is 439 bp long in length, and the third sequence is 829 bp long in length, respectively. Wild-type DNA was obtained from Promega (Madison, Wis.). Mutant DNA was extracted from a colon cancer cell line. The samples containing low-abundant mutant DNA were created by diluting mutant DNA with wild-type DNA. The abundance and the quantity of mutant DNA in the created samples were estimated based on the copy number of mutant DNA in the original samples and amounts of wild-type DNA added. In this example, the samples containing 1% was studied and enriched only once.

We designed 3 pairs of primer to generate these PCR products of three sizes. All forward primers had a T7 tail of 5'-GTAATACGACTCACTATAGG-5' (SEQ ID NO: 5) and all reverse primers had a T3 tail of 5'-AATTAACCCTCAC-TAAAGGG-3' (SEQ ID NO: 6). The sequences of the three pairs of the forward and reverse primers were:

F-Primer (158 bp):
(SEQ ID NO: 8)
5'-GTAATACGACTCACTATAGGCTTCCAGATAGCCCTGGACA-3';

R-primer (158 bp):
(SEQ ID NO: 9)
5'-AATTAACCCTCACTAAAGGGGCAGCATTTACTGCAGCTTG-3';

F-Primer (439 bp):
(SEQ ID NO: 13)
5'-GTAATACGACTCACTATAGGCTTCCAGATAGCCCTGGACA-3';

R-Primer (439 bp):
(SEQ ID NO: 14)
5'-AATTAACCCTCACTAAAGGGCATCTGAATCATCTAATAGGTCC-3'.

F-Primer (829 bp):
(SEQ ID NO: 15)
5'-GTAATACGACTCACTATAGGACACAGGAAGCAGATTCTGC-3';

R-Primer (829 bp):
(SEQ ID NO: 16)
5'-AATTAACCCTCACTAAAGGGCATCTGAATCATCTAATAGGTCC-3'.

The mini-sequencing extension primer was: 5'-CCT-CAAACAGCTCAAACCAAG-3' (SEQ ID NO: 10). The mutant probe and the normal competitor probe were: 5'-biotin-TCAAACCAAGTGAGAAGTA-3' (SEQ ID NO: 11) and 5'-TCAAACCAAGCGAGAAGTA-3' (SEQ ID NO: 12), respectively.

First PCR: 10 pmol of each forward and reverse primer, 0.2 mM of each dNTPs, 1×PCR buffer, 2 mM of $MgCl_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Enrichment: The first PCR products were incubated with a mixture of the mutant and normal probes for competing mutation-specific hybridization and extraction. 2 µL of the PCR product amplified above, 1×PCR buffer, 5 mM of EDTA, and 0.0 pmol/µL of the mutant probe and 0.075 pmol/µL of normal competitor probes were added to a tube in a total volume of 20 uL. The molar ratio of the normal to mutant probes used was 7.5. Hybridization of the probes with the PCR products was carried out by first denaturing DNA at 95° C. for 5 min, followed by slowly ramping down the temperature to 250 C at 0.04° C./sec. After hybridization, 5 µL of streptavidin-coated magnetic beads (Dynal Biotech, Oslo, Norway) in 20 µl 2× B&W buffer were added to the hybridization tube which was further incubated for 45 min at room temperature. The beads were washed 3 times by 180 µL of 1× TE buffer. Thereafter, 5 µL of 1×TE buffer was then added to resuspend the beads. The beads were heated at 95° C. for 5 min, followed by transferring the supernatant to a clean tube.

Second PCR: About 1 µL of the enriched DNA was used as templates for the second PCR amplification which utilized T7 of 5'-GTAATACGACTCACTATAGG-3' (SEQ ID NO: 5) and T3 of 5'-AATTAACCCTCACTAAAGGG-5' (SEQ ID NO: 6) as the forward and reverse primers, respectively. 10 pmol of forward and reverse primer, 0.2 mM of each dNTPs, 1×PCR buffer, 2 mM of $MgCl_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Mutation Analysis: The degree of enrichment was examined by a MALDI-TOF-based mini-sequencing assay. The products of the second PCR were first treated with Phosphatase and DNA exonecularse I for 30 min at 37° C., followed by 10 min at 80° C. 2.5 µL of the treated PCR products was mixed with 2.5 µL mixture of 0.025 mM of each ddATP, ddGTP and ddTTP, 0.1 mM of dCTP, 2× ThermoSequenase buffer, 1.5 mM $MgCl_2$, 1 pmol/µL of mini-sequencing primer, 0.2 u/µL of ThermoSequenase. Mini-sequencing was conducted under the condition of 2 min at 94° C. for preheat, followed by 60 cycles of 20 sec at 94° C., 20 sec at 50° C., 20 sec at 72° C. 10 µL of $NH_4OH$ treated ion exchange beads were incubated with the mini-sequencing products for desalting. The MALDI sample was prepared by mixing the extension products with the 3-HPA matrix. The sample was dried and then analyzed by MALDI-TOF. The degree of enrichment was determined by comparing the intensity of the peaks corresponding to the mutant and normal alleles.

Figure 6:
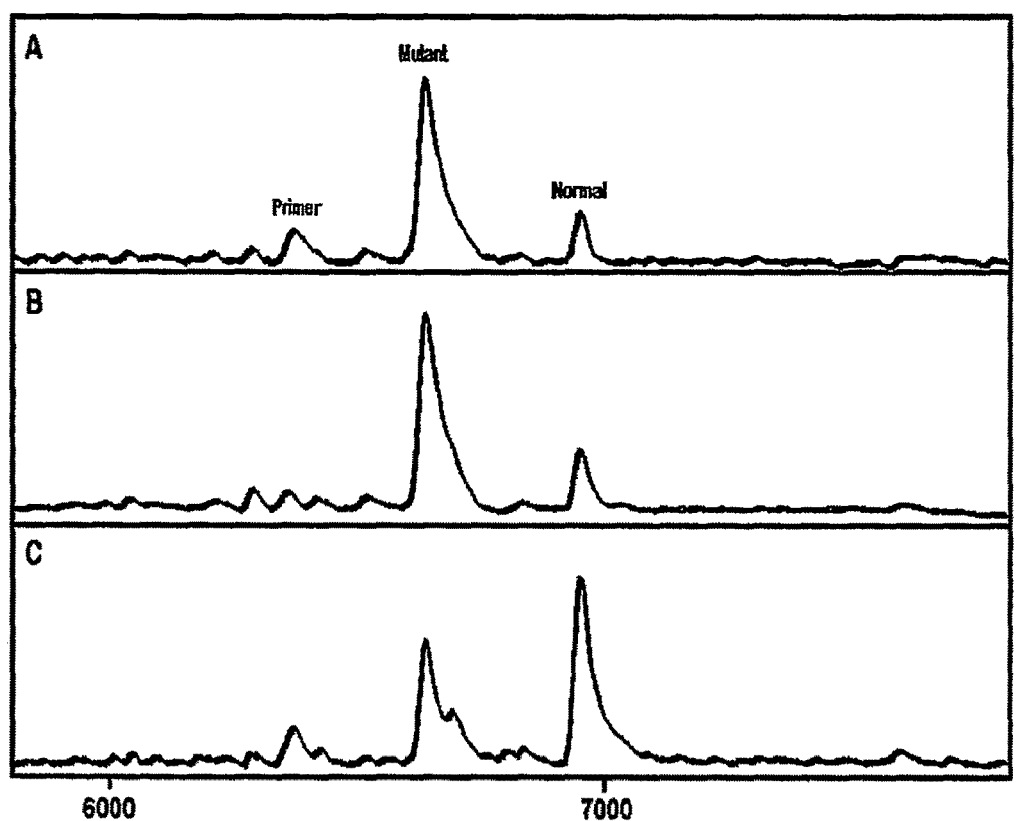
FIG. 6 illustrates the results of enriching the PCR products of 98 bp (A), 278 bp (B) and 575 bp (C), respectively, all of which contained the same C→T mutation at the first base of codon 1450 of APC. The samples contained 1% of mutant DNA and were enriched only once.

FIG. 6 displays enrichment of the PCR products of 158 bp (FIG. 6A), 439 bp (FIG. 6B) and 829 bp (FIG. 6C), respectively, all of which contained the same C→T mutation at the first base of codon 1450 of APC. All samples contained 1% of mutant DNA and were enriched only once. This result clearly shows that the degree of enrichment did not vary greatly with the DNA size, at least in the region of 158-829 bp, suggesting that this enrichment procedure could work well for a variety of PCR products of different size.

Example 5

This example is to demonstrate simultaneous enrichment of multiple target sequences. We addressed this issue by enriching 6 different mutant sequences under the same condition, four of which were p53 mutations (codon 190, 248, 267, and 274), the fifth of which was a k-ras mutation (codon 12), and the sixth of which was an APC mutation (codon 1450). Mutant DNA containing the k-ras and p53 mutations was extracted from the BAL samples of the patients with lung cancer and mutant DNA containing the APC mutation was extracted from a colon cancer cell line. The quantity of mutant DNA was determined. The samples containing low-abundant mutant DNA were created by diluting mutant DNA with wild-type DNA (Promega, Madison, Wis.). The abundance and the quantity of mutant DNA in the created samples were estimated based on the copy number of mutant DNA in the original samples and amounts of wild-type DNA added. In this example, the DNA samples containing 1%, or 0.1%, or 0.01% mutant DNA were studied.

In this study, we used multiplexed PCR to amplify 5 sequences covering these 6 sites (note that one of the sequences has two p53 mutation sites at codon 267 and 274). The first PCR utilizes 5 pairs of primers, each of which has a target-specific part and a universal tail part. The target-specific part amplified the target sequence, while the tail part introduced a sequence for the second PCR. The T7 sequence was used as the tail part of the forward primers, while the T3 sequence was used as the tail part of the reverse primers. The sequences of these primers were:

```
F-primer of K-ras:
                                        (SEQ ID NO: 1)
5'-GTAATACGACTCACTATAGGAGGCCTGCTGAAAATGACTG-3';

R-primer of K-ras:
                                        (SEQ ID NO: 2)
5'-AATTAACCCTCACTAAAGGGTTGGATCATATTCGTCCACAA-3';

F-primer of APC:
                                        (SEQ ID NO: 8)
5'-GTAATACGACTCACTATAGGCTTCCAGATAGCCCTGGACA-3'

R-Primer of APC:
                                        (SEQ ID NO: 9)
5'-AATTAACCCTCACTAAAGGGGCAGCATTTACTGCAGCTTG-3'

F-primer of p53 (codon 190):
                                        (SEQ ID NO: 17)
5'-GTAATACGACTCACTATAGGCAGTTGCAAACCAGAC CTCA-3'

R-primer of p53 (codon 190):
                                        (SEQ ID NO: 18)
5'-AATTAACCCTCACTAAAGGGCAGATAGCGATGGTGA GCAG-3';

F-primer of p53 (codon 248):
                                        (SEQ ID NO: 19)
5'-GTAATACGACTCACTATAGGGGGTCAGAGGCAAGCA GAG-3'

R-primer of p53 (codon 248):
                                        (SEQ ID NO: 20)
5'-AATTAACCCTCACTAAAGGGTGGCTCTGACTGTACC ACCA-3';

F-primer of p53 (codon 267 and 274):
                                        (SEQ ID NO: 21)
5'-GTAATACGACTCACTATAGGTCTTGCGGAG ATTCTCTTCC-3';

R-primer of p53 (codon 267 and 274):
                                        (SEQ ID NO: 22)
5'-AATTAACCCTCACTAAAGGGGACAAGGGTG GTTGGGAGTA-3';
```

First PCR: 2.5 pmol of each forward and reverse primer, 0.2 mM of each dNTPs, 1×PCR buffer, 2 mM of MgCl$_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Enrichment: The first PCR products were incubated with a mixture of the mutant and normal probes for competing mutation-specific hybridization and extraction. In this example, PCR products were enriched using 6 pairs of probes, each of which targeted one mutation site. 2 µL of the PCR product amplified above, 1×PCR buffer, 5 mM of EDTA, and 0.01 pmol/µL of each mutant probe and 0.075 pmol/µL of each normal competitor probe were added to the reaction tube in a total volume of 20 uL. The molar ratio of a normal competitor to its corresponding mutant probe used was 7.5. Hybridization of the probes with the PCR products was carried out by first denaturing DNA at 95° C. for 5 min, followed by slowly ramping down the temperature to 250 C at 0.04° C./sec. After hybridization, 5 µL of streptavidin-coated magnetic beads (Dynal Biotech, Oslo, Norway) in 20 µl 2× B&W buffer were added to the hybridization tube which was further incubated for 45 min at room temperature. The beads were washed 3 times by 180 µL of 1× TE buffer. Thereafter, 5 µL of 1×TE buffer was then added to resuspend the beads. The beads were heated at 95° C. for 5 min, followed by transferring the supernatant to a clean tube. The sequences of 6 pairs of mutant and normal competitor probes used were:

```
Mutant probe of K-ras:
5'-biotin- TTGGAGCTTGTGGCGTAG-3';    (SEQ ID NO: 3)

Normal Competitor Probe of K-ras:
5'- TTGGAGCTGGTGGCGTAG -3';          (SEQ ID NO: 4)

Mutant probe of APC:
5'-biotin- TCAAACCAAGTGAGAAGTA-3';   (SEQ ID NO: 11)

Normal Competitor Probe of APC:
5'- TCAAACCAAGCGAGAAGTA -3';         (SEQ ID NO: 12)

Mutant Probe of p53 (codon 190):
5'-biotin-CTGAGGAAGGGCCAGA-3';       (SEQ ID NO: 23)

Normal Competitor Probe of p53 (codon 190):
5'-CTGAGGAGGGGCCAGA-3';              (SEQ ID NO: 24)

Mutant Probe of p53 (codon 248):
5'-biotin-GGCCTCCAGTTCATGC-3';       (SEQ ID NO: 25)

Normal Competitor Probe (codon 248):
5'-GGCCTCCGGTTCATGC-3';              (SEQ ID NO: 26)

Mutant Probe of p53 (codon 267):
5'-biotin-CTGTTCGGTCCCAGTA-3';       (SEQ ID NO: 27)

Normal Competitor Probe of p53 (codon 267):
5'-CTGTTCCGTCCCAGTA-3';              (SEQ ID NO: 28)

Mutant Probe of p53 (codon 274):
5'-biotin-GCACAAAAACGCACCTC-3';      (SEQ ID NO: 29)

Normal Competitor Probe of p53 (codon 274):
and

5'-GCACAAACACGCACCTC-3';             (SEQ ID NO: 30)
```

Second PCR: About 1 uL of the enriched DNA was used as templates for the second PCR amplification which utilized T7 of 5'-GTAATACGACTCACTATAGG-3' (SEQ ID NO: 5) and T3 of 5'-AATTAACCCTCACTAAAGGG-3' (SEQ ID NO: 6) as the forward and reverse primers, respectively. 10 pmol of forward and reverse primer, 0.2 mM of each dNTPs, 1×PCR buffer, 2 mM of MgCl$_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Mutation Analysis: The degree of enrichment was examined by a MALDI-TOF-based mini-sequencing assay. The products of the second PCR were first treated with Phosphatase and DNA exonecularse I for 30 min at 37° C., followed by 10 min at 80° C. 2.5 µL of the treated PCR products was mixed with 2.5 µL mixture of 0.025 mM of each ddATP, ddGTP and ddTTP, 0.1 mM of dCTP, 2× ThermoSequenase buffer containing 1.5 mM MgCl$_2$, 1 pmol/µL of each mini-sequencing primer, 0.2 u/µL of ThermoSequenase. Mini-sequencing was conducted under the condition of 2 min at 94° C. for preheat, followed by 60 cycles of 20 sec at 94° C., 20 sec at 50° C., 20 sec at 72° C. 10 µL of NH$_4$OH treated ion exchange beads were incubated with the mini-sequencing products for desalting. The MALDI sample was prepared by mixing the extension products with the 3-HPA matrix. The sample was dried and then analyzed by MALDI-TOF. The degree of enrichment was determined by comparing the intensity of the peaks corresponding to the mutant and normal alleles. In this example, we used six mini-sequencing primers, each of which targeted one of the six mutation sites. The sequences of the mini-sequencing extension primer are:

```
Mini-Sequencing Extension Primer of k-ras:
5'-CAAGGCACTCTTGCCTACGCCA-3';      (SEQ ID NO: 7)

Mini-Sequencing Extension Primer of APC:
5'-CCTCAAACAGCTCAAACCAAG-3';       (SEQ ID NO: 10)

Mini-Sequencing Extension Primer of p53
(codon 190):
5'-TGCTCTTAGGTCTGGCCC-3';          (SEQ ID NO: 31)

Mini-Sequencing Extension Primer of p53
(codon 248):
5'-TGCATGGGCGGCATGAAC-3';          (SEQ ID NO: 32)

Mini-Sequencing Extension Primer of p53
(codon 267):
5'-CGCACCTCAAAGCTGTTC-3';          (SEQ ID NO: 33)

Mini-Sequencing Extension Primer of p53
(codon 274):
5'-TCCCAGGACAGGCACAAA-3';          (SEQ ID NO: 34)
```

Figure 7:
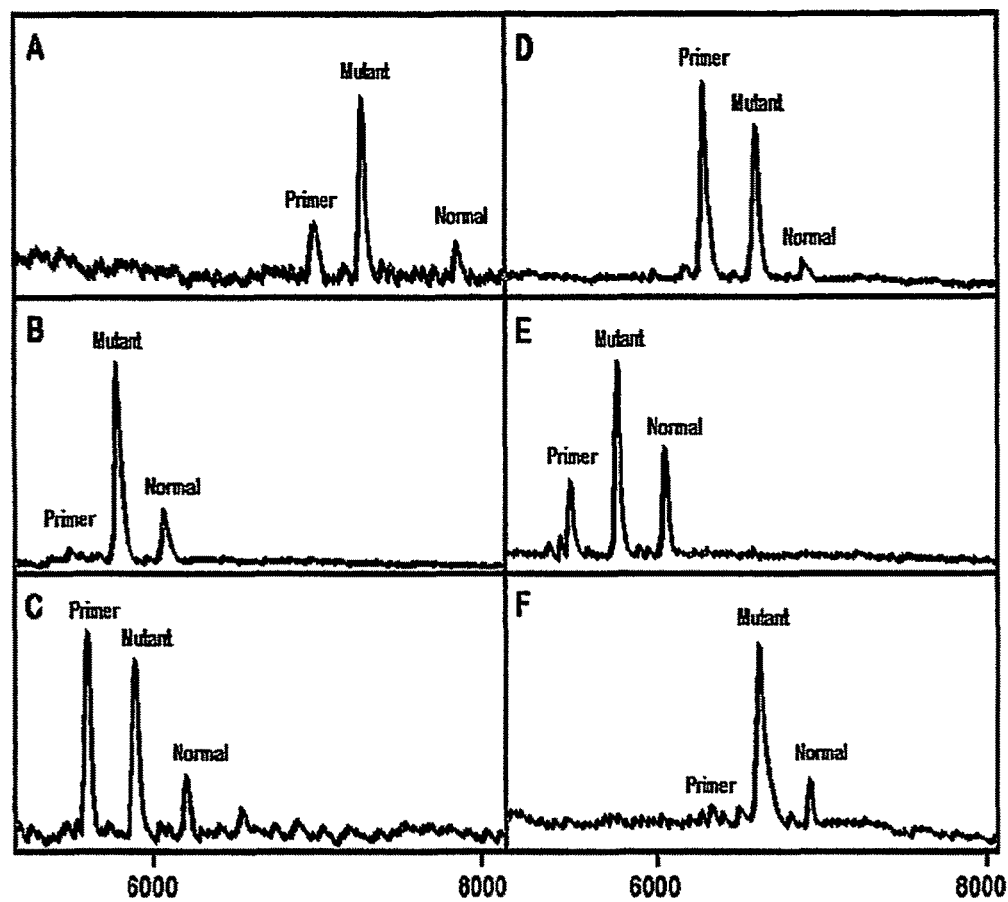
FIG. 7 illustrates the result of surveying the status of mutations in six DNA samples. Each sample contained 0.1% of mutant DNA and was enriched with two cycles of hybridization. Sample (A) contained a G→T mutation in the first base of codon 12 of k-ras; Sample (B) contained a C→T mutation in the second base of codon 190 of p53; Sample (C) contained a C→T mutation in the first base of codon 248 of p53; Sample (D) contained a G→C mutation in the second base of codon 267 of p53; Sample (E) contained a G→T mutation in the first base of codon 274 of p53; and Sample (F) contained a C→T mutation in the second base of codon 1450 of APC, respectively. Note that the correct mutation was identified from each sample and that no false-positive identification was seen.
Figure 8:
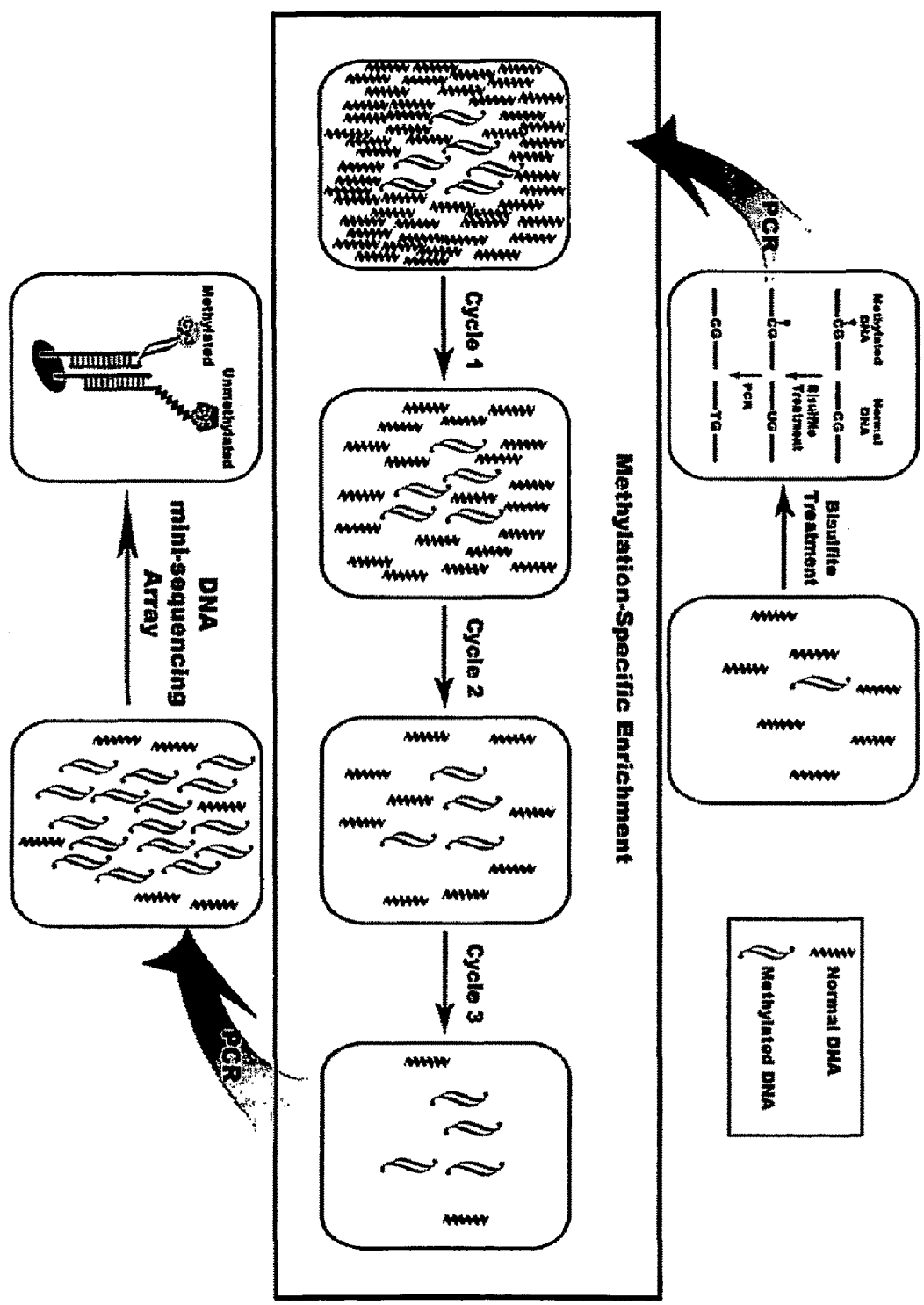
FIG. 8 is a schematic representation illustrating another preferred embodiment according to the present invention.

FIG. 7 displays the result of detecting the mutations in six samples, each of which had 0.1% of mutant DNA and was enriched twice. It was seen that the correct mutation was detected from each sample and no false-positives were detected. The correct mutations were also detected from the samples containing 0.01% of mutant DNA using three cycles of hybridization (data not shown).

Example 6

This example is to demonstrate methylation-specific enrichment. Methylation-specific enrichment was studied by enriching a methylated sequence of the ER gene. Positive control methylated DNA was created by treating normal DNA with SssI Methylase (New England Biolabs, MA) by using the suggested procedure, converting the cytosine at each CpG site to a methylated cytosine. Samples containing both methylated and unmethylated DNA were created by spiking methylated DNA into normal DNA, in which the abundance and the quantity of methylated DNA were estimated based on the copy number of methylated DNA in the original samples and amounts of unmethylated DNA added. The samples containing 0.1% and 0.01% of methylated DNA were studied and 20 copies of methylated DNA were used in each sample.

Bisulfite Treatment: We used the standard bisulfite treatment method to treat the samples DNA. 1 µg of salmon sperm DNA was first added to the DNA sample as carrier, followed by denaturing DNA in the presence of NaOH at 42° C. for 20 min. The freshly prepared bisulfite solution was added to the denatured DNA sample, followed by incubating the mixing solution in dark at 55° C. Thereafter, the treated sample was desulfonated, neutralized, and purified. The treated DNA was stored at −20° C.

First PCR: After bisulfite treatment, each sample was subjected to the first PCR. The primers of this PCR had a target-specific part and a universal tail of T7 (forward) or T3 (reverse). The target-specific part amplified a methylated sequence of ER, while the tail part introduced a sequence for the second PCR. The sequences of the forward and reverse primers were: 5'-GTAATACGACTCACTATAGGGGTG-TATTTGGATAGTAGTAAGTTTGT-3' (SEQ ID NO: 35) and 5'-AATTAACCCTCACTAAAGGGCTAT-TAAATAAAAAAAAACCCCCCAAACC-3'(SEQ ID NO: 36), respectively. 10 pmol of each forward and reverse primer, 0.2 mM of each dNTPs, 1×PCR buffer, 2 mM of MgCl$_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Enrichment: The first PCR products were incubated with a mixture of the methylation and unmethylated competitor probes for competing methylation-specific hybridization and extraction. 2 µL of the PCR product amplified above, 1×PCR buffer, 5 mM of EDTA, and 0.01 pmol/µL of the methylation and 0.075 pmol/µL of the unmethylated competitor probes were added to a tube in a total volume of 20 uL. The molar ratio of the unmethylated competitor to methylated probes used was 7.5. Hybridization of the probes with the PCR products was carried out by first denaturing DNA at 95° C. for 5 min, followed by slowly ramping down the temperature to 25° C. at 0.04° C./sec. After hybridization, 5 µL of streptavidin-coated magnetic beads (Dynal Biotech, Oslo, Norway) in 20 µl 2× B&W buffer were added to the hybridization tube which was further incubated for 45 min at room temperature. The beads were washed 3 times by 180 µL of 1× TE buffer. Thereafter, 5 µL of 1×TE buffer was then added to resuspend the beads. The beads were heated at 95° C. for 5 min, followed by transferring the supernatant to a clean tube. The sequence of the methylation and unmethylated competitor probes were 5'-biotin-ACGAGTTTAACGTCGCGG-3' (SEQ ID NO: 37) and 5'-ATGAGTTTAATGTTGTGG-3' (SEQ ID NO: 38), respectively.

Second PCR: About 1 uL of the enriched DNA was used as templates for the second PCR amplification which utilized T7 of 5'-GTAATACGACTCACTATAGG-3' (SEQ ID NO: 5) and T3 of 5'-AATTAACCCTCACTAAAGGG-3' (SEQ ID NO: 6) as the forward and reverse primers, respectively. 10 pmol of forward and reverse primer, 0.2 mM of each dNTPs, 1×PCR buffer, 2 mM of MgCl$_2$, 0.05 u/µL of TaqGold DNA polymerase, in a total reaction volume of 20 µL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension.

Methylation analysis: The degree of enrichment was examined by a MALDI-TOF-based mini-sequencing assay. The products of the second PCR were first treated with Phosphatase and DNA exonecularse I for 30 min at 37° C., followed by 10 min at 80° C. 2.5 µL of the treated PCR products was mixed with 2.5 µL mixture of 0.025 mM of each ddATP, ddGTP and ddTTP, 0.1 mM of dCTP, 2× ThermoSequenase buffer containing 1.5 mM MgCl$_2$, 1 pmol/µL of mini-sequencing primer, 0.2 u/µL of ThermoSequenase. Mini-sequencing was conducted under the condition of 2 min at 94° C. for preheat, followed by 60 cycles of 20 sec at 94° C., 20 sec at 50° C., 20 sec at 72° C. The mini-sequencing extension primer was 5'-CCCTCRAAATAATTATACAC-3' (SEQ ID NO: 39). 10 µL of NH₄OH treated ion exchange beads were incubated with the mini-sequencing products for desalting. The MALDI sample was prepared by mixing the extension products with the 3-HPA matrix. The sample was dried and then analyzed by MALDI-TOF. The degree of enrichment was determined by comparing the intensity of the peaks corresponding to the mutant and normal alleles.

Figure 10:
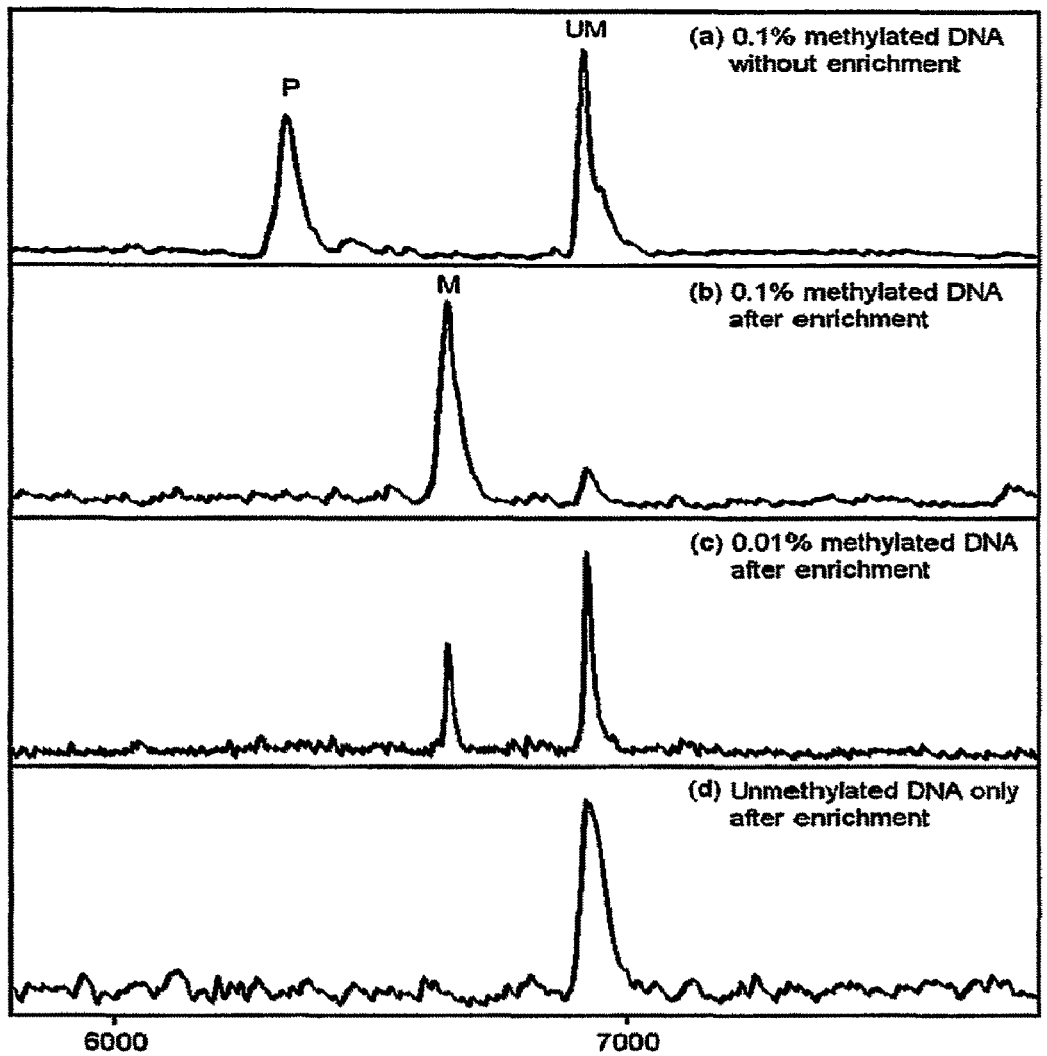
FIG. 10 illustrates the results of detecting methylated DNA with the MMPA method under different conditions, (a) assaying a sample containing 0.1% of methylated DNA without methylation-specific enrichment; (b) assaying a sample containing 0.1% of methylated DNA with methylation-specific enrichment; (c) assaying a sample containing 0.01% of methylated DNA with methylation-specific enrichment; and (d) assaying a sample containing no methylated DNA with methylation-specific enrichment.

FIG. 10 displays the result of this study, where the peaks labeled by P, M, and UM correspond to the primer, the extension products of the methylated and unmethylated alleles, respectively. FIGS. 10a and 10b display the result of detecting a methylated sequence of ER in a 1;000 folds more excess of unmethylated DNA without and with methylation-specific enrichment, respectively. No methylated DNA was detected without methylation-specific enrichment (FIG. 10a), while methylated DNA was clearly detected with methylation-specific enrichment (FIG. 10b), demonstrating the effectiveness of enriching methylated DNA by methylation-specific hybridization. FIG. 10c displays the result of successfully detecting 0.01% of methylated ER, establishing that MMPA could detect 0.01% of methylated DNA. It is noted that the specificity of MMPA is excellent, as demonstrated by assaying a sample containing only unmethylated DNA (FIG. 10d) using the same procedure, where no peak corresponding to methylated DNA was seen.

Example 7

This example is to demonstrate balancing the yield of different PCR products using the sequence-specific extraction strategy. In this example, 10 sequences of the BRAF, K-ras, p53, and APC genes were amplified by the first round PCR that used 10 pairs of primers, each of which has a target-specific part and a universal tail part. The target-specific part amplifies the target sequence, while the tail part introduces a sequence for the second PCR. The T7 and T3 sequences were used as the tail part of the forward and reverse primers, respectively. 50 ng of human genomic DNA were used as template. 2.5 pmol of each forward and reverse primer, 0.2 mM of each dNTPs, 1×PCR buffer, 2 mM of MgCl₂, 0.05 u/µL of TaqGold DNA polymerase, in a total reaction volume of 20 µL, were used in the PCR which was carried out first by denaturing DNA at 95° C. for 10 min, followed by 38 cycles of 60 sec at 95° C., 60 sec at 58° C., 60 sec at 72° C., finally with a 5 min at 72° C. for extension. The sequences of these 10 pairs of primers were:

```
F-Primer of BRAF:
                                        (SEQ ID NO: 40)
5'-GTAATACGACTCACTATAGGTGCTTGCTCTGATAGGAAA AT
GA-3';

R-Primer of BRAF:
                                        (SEQ ID NO: 41)
5'-AATTAACCCTCACTAAAGGGCCACAAAATGGATCCAGA CAAC-3';

F-Primer of p53 (codon 190):
                                        (SEQ ID NO: 17)
5'-GTAATACGACTCACTATAGGCAGTTGCAAACCAGAC CTCA-3';

R-primer of p53 (codon 190):
                                        (SEQ ID NO: 18)
5'-AATTAACCCTCACTAAAGGGCAGATAGCGATGGTGA GCAG-3';

F-Primer of p53 (codon 248):
                                        (SEQ ID NO: 19)
5'-GTAATACGACTCACTATAGGGGGTCAGAGGCAAGC AGAG-3';

R-Primer of p53 (codon 248):
                                        (SEQ ID NO: 20)
5'-AATTAACCCTCACTAAAGGGTGGCTCTGACTGTACC ACCA-3';

F-Primer of p53 (codon 267 and 274):
                                        (SEQ ID NO: 21)
5'-GTAATACGACTCACTATAGGTCTTGCGGAG ATTCTCTTCC-3';

R-primer of p53 (codon 267 and 274):
                                        (SEQ ID NO: 22)
5'-AATTAACCCTCACTAAAGGGGACAAGGGT GGTTGGGAGTA-3';

F-Primer of K-ras:
                                        (SEQ ID NO: 1)
5'-GTAATACGACTCACTATAGGAGGCCTGCTGAAAATGACTG-3';

R-Primer of K-ras:
                                        (SEQ ID NO: 2)
5'-AATTAACCCTCACTAAAGGGTTGGATCATATTCGTCCACAA-3';

F-Primer of APC (codon 876):
                                        (SEQ ID NO: 42)
5'-TAATACGACTCACTATAGGTCTAGGCAACTACCAT CAG-3';

R-Primer of APC (codon 876):
                                        (SEQ ID NO: 43)
5'-AATTAACCCTCACTAAAGGGGAGGTATGAATGGC TGACAC-3';

F-Primer of APC (codon 1114):
                                        (SEQ ID NO: 44)
5'-GTAATACGACTCACTATAGGCCAACCACATTTTGG ACAGC-3';

R-Primer of APC (codon 1114):
                                        (SEQ ID NO: 45)
5'-AATTAACCCTCACTAAAGGGTCTTCTTGACACA AA GACTG
GC-3';

F-primer of APC (codon 1306):
                                        (SEQ ID NO: 46)
5'-GTAATACGACTCACTATAGGACACAGGAAGCAGATTCTGC-3';

R-Primer of APC (codon 1306):
                                        (SEQ ID NO: 47)
5'-AATTAACCCTCACTAAAGGGCTATCAAGTGAACT GACAGAAG-3';

F-Primer of APC (codon 1450):
                                        (SEQ ID NO: 8)
5'-GTAATACGACTCACTATAGGCTTCCAGATAGCCCT GGACA-3';

R-primer of APC (codon 1450):
                                        (SEQ ID NO: 9)
5'-AATTAACCCTCACTAAAGGGGCAGCATTTAGTGCA GCTTG-3';

F-Primer of APC (codon 1554):
                                        (SEQ ID NO: 48)
5'-GTAATACGACTCACTATAGGGGGAATGAAACAGA ATCAGAGC-3';

R-Primer of APC (codon 1554):
                                        (SEQ ID NO 49)
5'-AATTAACCCTCACTAAAGGGCATCTGAATCATCT AATAGGT
CC-3'.
```

Sequence-Specific Extraction: The products of the first PCR were mixed with 10 sequence-specific probes for extraction, each of which hybridized with one of the amplified sequences and extracted this sequence. 2 µL of the PCR product amplified above, 1×PCR buffer, 5 mM of EDTA, and 0.01 pmol/µL of each sequence-specific probe were added to a tube in a total volume of 20 uL. Hybridization of the probes with the PCR products was carried out by first denaturing DNA at 95° C. for 5 min, followed by slowly ramping down the temperature to 25° C. at 0.04° C./sec. After hybridization, 5 µL of streptavidin-coated magnetic beads (Dynal Biotech, Oslo, Norway) in 20 µl 2× B&W buffer were added to the hybridization tube which was further incubated for 45 min at room temperature. The beads were washed 3 times by 180 μL of 1× TE buffer. Thereafter, 5 μL of 1×TE buffer was then added to resuspend the beads. The beads were heated at 95° C. for 5 min, followed by transferring the supernatant to a clean tube. The sequences of these sequence-specific probes were:

```
K-ras:
5'-BIOTIN-TTGGAGCTGGTGGCGTAG-3';         (SEQ ID NO: 50)

p53 (codon 190):
5'-BIOTIN-ATCTTATCCGAGTGGAAGG-3';        (SEQ ID NO: 51)

p53 (codon 248):
5'-BIOTIN-CCTGCATGGGCGGCATGA-3';         (SEQ ID NO: 52)

p53 (codon 267):
5'-BIOTIN-CTCTCCCAGGAGAGGCAC-3';         (SEQ ID NO: 53)

APC (codon 876):
5'-BIOTIN-CTTCAAAGCGAGGTTTGC-3';         (SEQ ID NO: 54)

APC (codon 1114):
5'-BIOTIN-GAAACAAATCGAGTGGGT-3';         (SEQ ID NO: 55)

APC (codon 1306):
5'-BIOTIN-CAGTGTCACAGCACCCTA-3';         (SEQ ID NO: 56)

APC (codon 1450):
5'-BIOTIN-CCACCACCTCCTCAAACAG-3';        (SEQ ID NO: 57)

APC (codon 1554):
5'-BIOTIN-GAGGCAGAAAAAACTATTGA-3';       (SEQ ID NO: 58)

BRAF:
5'-BIOTIN-CGAGATTTCACTGTAGCT-3';         (SEQ ID NO: 59)
```

Second PCR: 0.5 uL of first run PCR product or about 1 uL of the enriched DNA was used as templates for the second PCR amplification which utilized T7 of 5'-D4-GTAATAC-GACTCACTATAGG-3' (SEQ ID NO: 60) and T3 of 5'-AAT-TAACCCTCACTAAAGGG-3' (SEQ ID NO: 6) as the forward and reverse primers, respectively. 10 pmol of forward and reverse primer, 0.2 mM of each dNTPs, 1×PCR buffer, 2 mM of $MgCl_2$, 0.05 u/μL of TaqGold DNA polymerase, in a total reaction volume of 20 μL, were used in the PCR which was carried out first by denaturing DNA at 95° C. for 10 min, followed by 38 cycles of 30 sec at 95° C., 30 sec at 58° C., 30 sec at 72° C., finally with a 5 min at 72° C. for extension. The T7 primer had a fluorescence tag, allowing for the fragment analysis of the final PCR products with a DNA sequencer.

Figure 11:
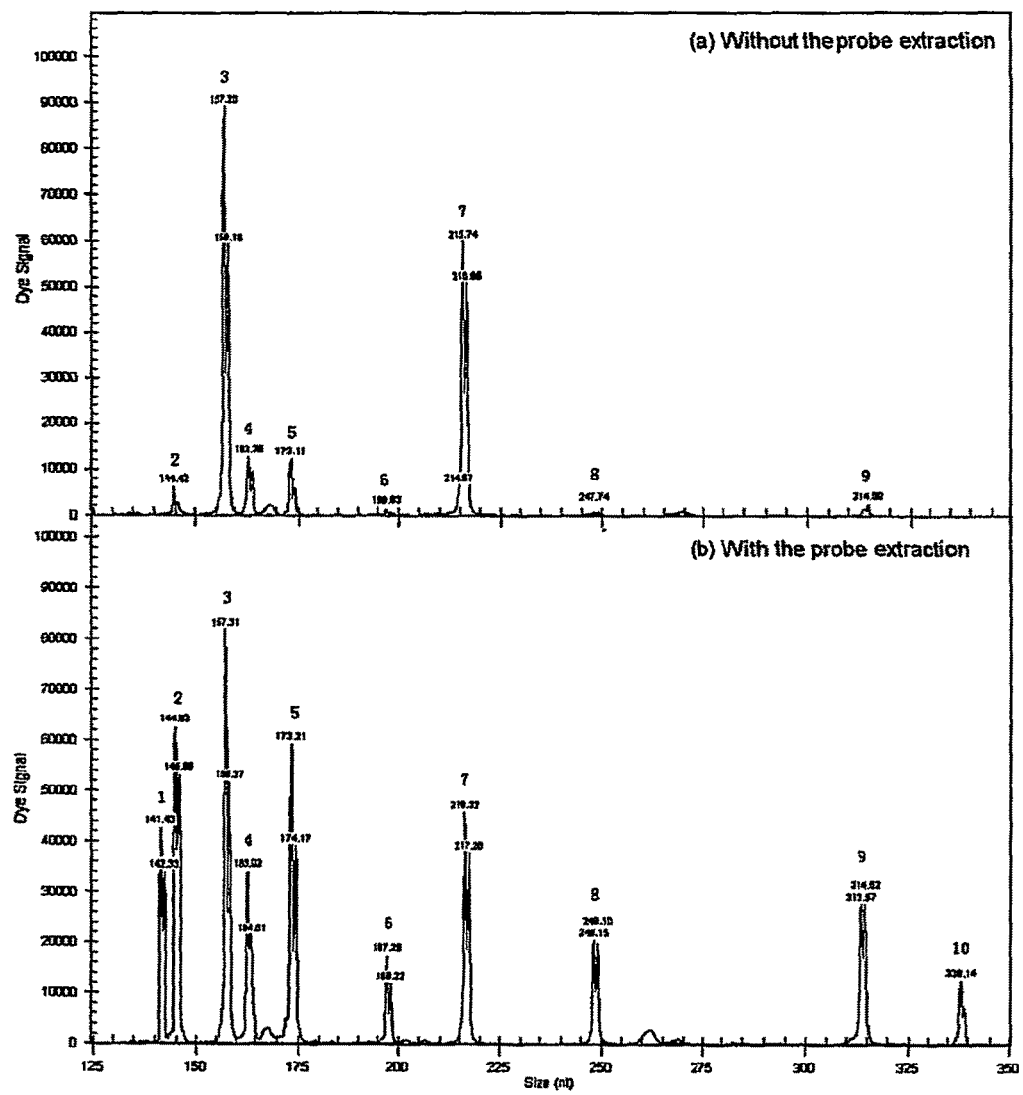
FIG. 11 illustrates DNA fragments analysis spectra of the PCR products produced (a) without a sequence-specific extraction step between two rounds of PCR; and (b) with a sequence-specific extraction step.

FIG. 11 displays the result of this study, where the peaks labeled by 1, 2 ... 10 correspond to 10 sequences amplified, respectively. FIG. 11a is a fragment analysis spectrum of the PCR products amplified without the use of a probe extraction step between two rounds of PCR. Clearly, the yield of the PCR products varied greatly and several sequences were even not detectable. FIG. 11b displays the result after adding a probe extraction step between two rounds of PCR and optimizing the molar ratio of 10 probes, where that the yield of each PCR product was similar, demonstrating the effectiveness of using a probe extraction procedure to balance the product yield of multiplexed PCR. It is noted that probe extraction can be a general method to improve multiplexed PCR.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for surveying the status of multiple mutation markers in a large background of wild-type DNA, the method comprising:

providing a sample including mutant DNA and wild-type DNA, the mutant DNA including mutations;

amplifying the sample by a first PCR to generate DNA fragments containing the mutation sites; wherein the first PCR is multiplexed PCR utilizing two or more pairs of PCR primers, wherein each pair of primers includes a forward primer and a reverse primer, wherein each pair of primers is adapted to amplify a sequence containing one or more of the mutation sites and wherein each primer includes both a target-specific part and a universal tail part, wherein the target-specific part flanks the sequence to allow for amplification of the sequence and the sequence of the universal tail part is the same for all forward and reverse primers, wherein the universal tail cannot bind to human genomic sequence;

enriching the mutant DNA fragments containing the mutations from the amplicons of the multiplexed PCR simultaneously by performing one or multiple mutant-specific enrichment cycles including competing mutation-specific hybridization and extraction to thereby form an enriched system;

amplifying the enriched system by a second PCR to generate sufficient amounts of mutant DNA for detection; and simultaneously surveying the status of the target mutation sites.

2. The method of claim 1 wherein the mutation sites include one or more single-base (i) substitutions, (ii) insertions, (iii) deletions and (iv) combinations thereof.

3. The method of claim 1 wherein the sample is obtained from clinical biospecimens collected from patients, the biospecimens selected from the group consisting of human tumor tissues, peripheral blood, stool, urine, bodily fluids, washing fluids associated with medical procedures, and combinations thereof.

4. The method of claim 3 wherein the molar ratio of the wild-type DNA to the mutant DNA is from about 2:1 to about 100,000:1 in the DNA sample.

5. The method of claim 1 wherein the mutant-specific enrichment cycles are selected from the group consisting of (i) depleting wild-type DNA, (ii) selectively capturing mutant DNA, and (iii) a combination of (i) and (ii).

6. The method of claim 1 wherein enriching of the mutant DNA fragments containing the mutations is performed by mutation-specific hybridization and extraction, wherein a plurality of mutant-specific probes are contacted with the DNA fragments of the first PCR under hybridization conditions wherein each mutant-specific probe preferentially forms hybrids with a mutant sequence, wherein the mutant-specific probes are further attached to a first binding molecule that is capable of binding to a second binding molecule that is attached to a solid support, and wherein after hybridization, the hybrids are captured by the solid support containing the second binding molecule, wherein after washing the solid support, the captured DNA fragments are released by heating or by using a conventional chemical or biological method; and wherein the DNA fragments released from the solid support are subjected to additional cycles of the mutation-specific hybridization and extraction when further enrichment is needed.

7. The method of claim 6 wherein the number of mutant-specific enrichment cycles performed ranges from one cycle to five cycles.

8. The method of claim 7, wherein the number of cycles is one.

9. The method of claim 7, wherein the number of cycles is two or more.

10. The method of claim 9 wherein the mutation-specific hybridization and extraction is repeated, wherein the DNA fragments extracted by the solid support are released from the solid support and further subjected to additional cycles of the mutation-specific enrichment hybridization and extraction.

11. The method of claim 6 wherein the mutant-specific probes are selected from the group consisting of oligonucleotides, peptide nucleic acids, locked nucleic acids, and combinations thereof.

12. The method of claim 6 wherein the first binding molecule is selected from the group consisting of biotin, streptavidin, and combinations thereof, and the second binding molecule is selected from the group consisting of streptavidin, biotin, and combinations thereof.

13. The method of claim 1 wherein enriching of the DNA fragments containing the mutation sites is performed by competing mutation-specific hybridization and extraction, wherein a plurality of mutant-specific probes and normal-competitor probes are contacted with the DNA fragments of the first PCR under hybridization conditions wherein each mutant-specific probe preferentially forms hybrids with a mutant sequence while its corresponding normal competitor probe preferentially forms hybrids with the corresponding wild-type sequence, wherein the mutant-specific probes are further attached to a first binding molecule that is capable of binding to a second binding molecule that is attached to a solid support, and wherein after hybridization, the hybrids are captured by the solid support containing the second binding molecule, wherein after washing the solid support, the captured DNA fragments are released by heating or by using a conventional chemical or biological method; and wherein the DNA fragments released from the solid support are subjected to additional cycles of the mutation-specific hybridization and extraction when further enrichment is needed.

14. The method of claim 13 wherein the number of competing mutation-specific hybridization and extraction cycles performed ranges from one cycle to five cycles.

15. The method of claim 14 wherein the number of cycles is one.

16. The method of claim 14 wherein the number of cycles is two or more.

17. The method of claim 16 wherein the competing mutation-specific hybridization and extraction is repeated, wherein the DNA fragments extracted by the solid support are released from the solid support and further subjected to additional cycles of the competing mutation-specific enrichment and extraction.

18. The method of claim 13 wherein the mutant-specific probes and the normal competitor probes are each selected from the group consisting of oligonucleotides, peptide nucleic acids, locked nucleic acids, and combinations thereof.

19. The method of claim 13 wherein the molar ratio of each mutant-specific probe to its corresponding normal competitor probe is from about 0.02:1 to about 10:1.

20. The method of claim 13 wherein the first binding molecule is selected from the group consisting of biotin, streptavidin, and combinations thereof and the second binding molecule is selected from the group consisting of streptavidin, biotin, and combinations thereof.

21. The method of claim 1 wherein the first PCR uses two or more pairs of primers, each pair of primers includes a forward primer and a reverse primer, each pair of primers including a universal tail, the second PCR is performed by contacting the enriched DNA fragments containing the mutations with universal primers, wherein the universal primers hybridize to the universal tails of the forward and reverse primers to amplify all enriched DNA fragments.

22. The method of claim 21 wherein the second PCR utilizes one universal primer when the universal tail of the forward and reverse primers of the first PCR is the same, and wherein the second PCR utilizes two universal primers when the universal tail of the forward and reverse primers of the first PCR are different, wherein the one universal primer matches the universal tail of the forward primers of the first PCR while the other universal primer matches to the universal tail of the reverse primers of the first PCR.

23. A method for producing sufficiently pure mutant DNA fragments for determining the mutation status at a plurality of DNA mutation sites in a large background of wild-type DNA, the method comprising: providing a DNA sample including both mutant DNA and wild-type DNA; amplifying DNA sequences including the mutation sites by multiplexed PCR to thereby produce amplicons; and enriching mutant DNA fragments having the mutations from the amplicons of the PCR simultaneously by competing mutation-specific hybridization and extraction;
wherein the multiplexed PCR utilizes two or more pairs of PCR primers, wherein each pair of the primers hybridize to a sequence containing one or more of the mutation sites for amplification of the sequence.

24. The method of claim 23 wherein the DNA mutations are selected from the group consisting of one or more single-base (i) substitutions, (ii) insertions, (iii) deletions, and (iv) combinations thereof.

25. The method of claim 23 wherein the DNA sample is obtained from clinical biospecimens collected from patients, the biospecimens selected from the group consisting of human tumor tissues, peripheral blood, stool, urine, bodily fluids, washing fluids associated with medical procedures, and combinations thereof.

26. The method of claim 23 wherein the molar ratio of the wild-type DNA to the mutant DNA is from about 2:1 to about 100,000:1 in the DNA sample.

27. The method of claim 23 wherein enriching mutant DNA fragments is performed by an operation selected from the group consisting of (i) depleting wild-type DNA, (ii) selectively capturing mutant DNA, and (iii) a combination of (i) and (ii).

28. The method of claim 23 wherein enrichment is performed by mutation-specific hybridization and extraction and such is performed by contacting a plurality of mutant-specific probes with the amplicons of the multiplexed PCR under hybridization conditions wherein mutant-specific probes preferentially form hybrids with mutant sequences, wherein the mutation-specific hybridization probes are further attached to a first binding molecule that is capable of binding to a second binding molecule that is attached to a solid support, and wherein after hybridization, the hybrids are captured by the solid support containing the second binding molecule, wherein after washing the solid support, the captured DNA fragments are released by heating or by using a conventional chemical or biological method; and wherein the DNA fragments released from the solid support are subjected to additional cycles of the mutation-specific hybridization and extraction when further enrichment is needed.

29. The method of claim 28 wherein the number of mutant-specific enrichment cycles performed ranges from one cycle to five cycles.

30. The method of claim 29, wherein the number of cycles is one.

31. The method of claim 29, herein the number of cycles is two or more.

32. The method of claim 31 wherein the mutation-specific hybridization and extraction is repeated, wherein the DNA fragments extracted by the solid support are released from the solid support and further subjected to additional cycles of the mutation-specific enrichment and extraction.

33. The method of claim 28 wherein the mutant-specific probes are selected from the group consisting of oligonucleotides, peptide nucleic acids, locked nucleic acids, and combinations thereof.

34. The method of claim 28 wherein the first binding molecule is selected from the group consisting of biotin, streptavidin, and combinations thereof, and the second binding molecule is selected from the group consisting of streptavidin, biotin, and combinations thereof.

35. The method of claim 23 wherein enrichment is performed by competing mutation-specific hybridization and extraction and such is performed by contacting a plurality of mutant-specific probes and normal competitor probes with the amplicons of the multiplexed PCR under hybridization conditions wherein each mutant-specific probe preferentially forms hybrids with a mutant sequence while its corresponding normal competitor probe preferentially form hybrids with the corresponding wild-type sequence, wherein the mutant-specific probes are further attached to a first binding molecule that is capable of binding to a second binding molecule that is attached to a solid support, and wherein after hybridization, the hybrids are captured by the solid support containing the second binding molecule, wherein after washing the solid support, the captured DNA fragments are released by heating or by using a conventional chemical or biological method; and wherein the DNA fragments released from the solid support are subjected to additional cycles of the mutation-specific hybridization and extraction when further enrichment is needed.

36. The method of claim 35 wherein the number of competing mutation-specific hybridization and extraction cycles performed ranges from one cycle to five cycles.

37. The method of claim 36 wherein the number of cycles is one.

38. The method of claim 36 wherein the number of cycles is two or more.

39. The method of claim 38 wherein the competing mutation-specific hybridization and extraction is repeated, wherein the DNA fragments extracted by the solid support are released from the solid support and further subjected to additional cycles of the competing mutation-specific enrichment hybridization and extraction.

40. The method of claim 35 wherein the mutant-specific probes and the normal competitor probes are each selected from the group consisting of oligonucleotides, peptide nucleic acids, locked nucleic acids, and combinations thereof.

41. The method of claim 35 wherein the molar ratio of each mutant-specific probe to its corresponding normal competitor probe is from about 0.02:1 to about 10:1.

42. The method of claim 35 wherein the first binding molecule is selected from the group consisting of biotin, streptavidin, and combinations thereof and the second binding molecule is selected from the group consisting of streptavidin, biotin, and combinations thereof.

43. A method for surveying the status of multiple mutation markers in a large background of wild-type DNA, the method comprising:

(a) providing a sample including mutant DNA and wild-type DNA, the mutant DNA including mutations;

(b) amplifying the sample from step (a) by a first PCR to generate DNA fragments containing the mutation sites;

(c) enriching the mutant DNA fragments from step (b) containing the mutations by performing one or multiple mutant-specific enrichment cycles to thereby form an enriched system;

(d) amplifying the enriched system from step (c) by a second PCR to generate sufficient amounts of mutant DNA for detection; and (e) surveying the status of the target mutation sites after completing the amplifying step (d).

* * * * *

```
                       SEQUENCE LISTING

<160> NUMBER OF SEQ ID NOS: 60

<210> SEQ ID NO 1
<211> LENGTH: 40
<212> TYPE: DNA
<213> ORGANISM: Homo sapiens

<400> SEQUENCE: 1
gtaatacgac tcactatagg aggcctgctg aaaatgactg                      40

<210> SEQ ID NO 2
<211> LENGTH: 41
<212> TYPE: DNA
<213> ORGANISM: Homo sapiens

<400> SEQUENCE: 2
aattaaccct cactaaaggg ttggatcata ttcgtccaca a                    41

<210> SEQ ID NO 3
<211> LENGTH: 18
<212> TYPE: DNA
<213> ORGANISM: Homo sapiens

<400> SEQUENCE: 3
ttggagcttg tggcgtag                                              18

<210> SEQ ID NO 4
<211> LENGTH: 18
```

```
<212> TYPE: DNA
<213> ORGANISM: Homo sapiens

<400> SEQUENCE: 4
ttggagctgg tggcgtag                                              18

<210> SEQ ID NO 5
<211> LENGTH: 20
<212> TYPE: DNA
<213> ORGANISM: Bacteriophage T7

<400> SEQUENCE: 5
gtaatacgac tcactatagg                                            20

<210> SEQ ID NO 6
<211> LENGTH: 20
<212> TYPE: DNA
<213> ORGANISM: Bacteriophage T3

<400> SEQUENCE: 6
aattaaccct cactaaaggg                                            20

<210> SEQ ID NO 7
<211> LENGTH: 23
<212> TYPE: DNA
<213> ORGANISM: Homo sapiens

<400> SEQUENCE: 7
caaggcactc ttgcctacgc cac                                        23

<210> SEQ ID NO 8
<211> LENGTH: 40
<212> TYPE: DNA
<213> ORGANISM: Homo sapiens

<400> SEQUENCE: 8
gtaatacgac tcactatagg cttccagata gccctggaca                      40

<210> SEQ ID NO 9
<211> LENGTH: 40
<212> TYPE: DNA
<213> ORGANISM: Homo sapiens

<400> SEQUENCE: 9
aattaaccct cactaaaggg gcagcattta ctgcagcttg                      40

<210> SEQ ID NO 10
<211> LENGTH: 21
<212> TYPE: DNA
<213> ORGANISM: Homo sapiens

<400> SEQUENCE: 10
cctcaaacag ctcaaaccaa g                                          21

<210> SEQ ID NO 11
<211> LENGTH: 19
<212> TYPE: DNA
<213> ORGANISM: Homo sapiens

<400> SEQUENCE: 11
tcaaaccaag tgagaagta                                             19

<210> SEQ ID NO 12
<211> LENGTH: 19
```

```
<212> TYPE: DNA
<213> ORGANISM: Homo sapiens

<400> SEQUENCE: 12
tcaaaccaag cgagaagta                                                 19

<210> SEQ ID NO 13
<211> LENGTH: 40
<212> TYPE: DNA
<213> ORGANISM: Homo sapiens

<400> SEQUENCE: 13
gtaatacgac tcactatagg cttccagata gccctggaca                          40

<210> SEQ ID NO 14
<211> LENGTH: 43
<212> TYPE: DNA
<213> ORGANISM: Homo sapiens

<400> SEQUENCE: 14
aattaaccct cactaaaggg catctgaatc atctaatagg tcc                      43

<210> SEQ ID NO 15
<211> LENGTH: 40
<212> TYPE: DNA
<213> ORGANISM: Homo sapiens

<400> SEQUENCE: 15
gtaatacgac tcactatagg acacaggaag cagattctgc                          40

<210> SEQ ID NO 16
<211> LENGTH: 43
<212> TYPE: DNA
<213> ORGANISM: Homo sapiens

<400> SEQUENCE: 16
aattaaccct cactaaaggg catctgaatc atctaatagg tcc                      43

<210> SEQ ID NO 17
<211> LENGTH: 40
<212> TYPE: DNA
<213> ORGANISM: Homo sapiens

<400> SEQUENCE: 17
gtaatacgac tcactatagg cagttgcaaa ccagacctca                          40

<210> SEQ ID NO 18
<211> LENGTH: 40
<212> TYPE: DNA
<213> ORGANISM: Homo sapiens

<400> SEQUENCE: 18
aattaaccct cactaaaggg cagatagcga tggtgagcag                          40

<210> SEQ ID NO 19
<211> LENGTH: 39
<212> TYPE: DNA
<213> ORGANISM: Homo sapiens

<400> SEQUENCE: 19
gtaatacgac tcactatagg gggtcagagg caagcagag                           39

<210> SEQ ID NO 20
<211> LENGTH: 40
```

```
<212> TYPE: DNA
<213> ORGANISM: Homo sapiens

<400> SEQUENCE: 20
aattaaccct cactaaaggg tggctctgac tgtaccacca                    40

<210> SEQ ID NO 21
<211> LENGTH: 42
<212> TYPE: DNA
<213> ORGANISM: Homo sapiens

<400> SEQUENCE: 21
gtaatacgac tcactatagg tcttgcggag attctctctt cc                 42

<210> SEQ ID NO 22
<211> LENGTH: 40
<212> TYPE: DNA
<213> ORGANISM: Homo sapiens

<400> SEQUENCE: 22
aattaaccct cactaaaggg gacaagggtg gttgggagta                    40

<210> SEQ ID NO 23
<211> LENGTH: 16
<212> TYPE: DNA
<213> ORGANISM: Homo sapiens

<400> SEQUENCE: 23
ctgaggaagg gccaga                                              16

<210> SEQ ID NO 24
<211> LENGTH: 16
<212> TYPE: DNA
<213> ORGANISM: Homo sapiens

<400> SEQUENCE: 24
ggcctccagt tcatgc                                              16

<210> SEQ ID NO 25
<211> LENGTH: 16
<212> TYPE: DNA
<213> ORGANISM: Homo sapiens

<400> SEQUENCE: 25
ggcctccggt tcatgc                                              16

<210> SEQ ID NO 26
<211> LENGTH: 16
<212> TYPE: DNA
<213> ORGANISM: Homo sapiens

<400> SEQUENCE: 26
ggcctccggt tcatgc                                              16

<210> SEQ ID NO 27
<211> LENGTH: 16
<212> TYPE: DNA
<213> ORGANISM: Homo sapiens

<400> SEQUENCE: 27
ctgttcggtc ccagta                                              16

<210> SEQ ID NO 28
<211> LENGTH: 16
```

<212> TYPE: DNA
<213> ORGANISM: Homo sapiens

<400> SEQUENCE: 28
ctgttccgtc ccagta                                                       16

<210> SEQ ID NO 29
<211> LENGTH: 17
<212> TYPE: DNA
<213> ORGANISM: Homo sapiens

<400> SEQUENCE: 29
gcacaaaaac gcacctc                                                      17

<210> SEQ ID NO 30
<211> LENGTH: 17
<212> TYPE: DNA
<213> ORGANISM: Homo sapiens

<400> SEQUENCE: 30
gcacaaacac gcacctc                                                      17

<210> SEQ ID NO 31
<211> LENGTH: 18
<212> TYPE: DNA
<213> ORGANISM: Homo sapiens

<400> SEQUENCE: 31
tgctcttagg tctggccc                                                     18

<210> SEQ ID NO 32
<211> LENGTH: 18
<212> TYPE: DNA
<213> ORGANISM: Homo sapiens

<400> SEQUENCE: 32
tgcatgggcg gcatgaac                                                     18

<210> SEQ ID NO 33
<211> LENGTH: 18
<212> TYPE: DNA
<213> ORGANISM: Homo sapiens

<400> SEQUENCE: 33
cgcacctcaa agctgttc                                                     18

<210> SEQ ID NO 34
<211> LENGTH: 18
<212> TYPE: DNA
<213> ORGANISM: Homo sapiens

<400> SEQUENCE: 34
tcccaggaca ggcacaaa                                                     18

<210> SEQ ID NO 35
<211> LENGTH: 47
<212> TYPE: DNA
<213> ORGANISM: Homo sapiens

<400> SEQUENCE: 35
gtaatacgac tcactatagg ggtgtatttg gatagtagta agtttgt                     47

<210> SEQ ID NO 36
<211> LENGTH: 49

```
<212> TYPE: DNA
<213> ORGANISM: Homo sapiens

<400> SEQUENCE: 36
aattaaccct cactaaaggg ctattaaata aaaaaaaacc ccccaaacc       49

<210> SEQ ID NO 37
<211> LENGTH: 18
<212> TYPE: DNA
<213> ORGANISM: Homo sapiens

<400> SEQUENCE: 37
acgagtttaa cgtcgcgg                                          18

<210> SEQ ID NO 38
<211> LENGTH: 18
<212> TYPE: DNA
<213> ORGANISM: Homo sapiens

<400> SEQUENCE: 38
atgagtttaa tgttgtgg                                          18

<210> SEQ ID NO 39
<211> LENGTH: 20
<212> TYPE: DNA
<213> ORGANISM: Homo sapiens

<400> SEQUENCE: 39
ccctcraaat aattatacac                                        20

<210> SEQ ID NO 40
<211> LENGTH: 43
<212> TYPE: DNA
<213> ORGANISM: Homo sapiens

<400> SEQUENCE: 40
gtaatacgac tcactatagg tgcttgctct gataggaaaa tga              43

<210> SEQ ID NO 41
<211> LENGTH: 42
<212> TYPE: DNA
<213> ORGANISM: Homo sapiens

<400> SEQUENCE: 41
aattaaccct cactaaaggg ccacaaaatg gatccagaca ac               42

<210> SEQ ID NO 42
<211> LENGTH: 38
<212> TYPE: DNA
<213> ORGANISM: Homo sapiens

<400> SEQUENCE: 42
taatacgact cactataggt ctaggcaact accatcag                    38

<210> SEQ ID NO 43
<211> LENGTH: 40
<212> TYPE: DNA
<213> ORGANISM: Homo sapiens

<400> SEQUENCE: 43
aattaaccct cactaaaggg gaggtatgaa tggctgacac                  40

<210> SEQ ID NO 44
<211> LENGTH: 40
```

```
<212> TYPE: DNA
<213> ORGANISM: Homo sapiens

<400> SEQUENCE: 44
gtaatacgac tcactatagg ccaaccacat tttggacagc                    40

<210> SEQ ID NO 45
<211> LENGTH: 42
<212> TYPE: DNA
<213> ORGANISM: Homo sapiens

<400> SEQUENCE: 45
aattaaccct cactaaaggg tcttcttgac acaaagactg gc                 42

<210> SEQ ID NO 46
<211> LENGTH: 40
<212> TYPE: DNA
<213> ORGANISM: Homo sapiens

<400> SEQUENCE: 46
gtaatacgac tcactatagg acacaggaag cagattctgc                    40

<210> SEQ ID NO 47
<211> LENGTH: 42
<212> TYPE: DNA
<213> ORGANISM: Homo sapiens

<400> SEQUENCE: 47
gtaatacgac tcactatagg gggaatgaaa cagaatcaga gc                 42

<210> SEQ ID NO 48
<211> LENGTH: 42
<212> TYPE: DNA
<213> ORGANISM: Homo sapiens

<400> SEQUENCE: 48
gtaatacgac tcactatagg gggaatgaaa cagaatcaga gc                 42

<210> SEQ ID NO 49
<211> LENGTH: 43
<212> TYPE: DNA
<213> ORGANISM: Homo sapiens

<400> SEQUENCE: 49
aattaaccct cactaaaggg catctgaatc atctaatagg tcc                43

<210> SEQ ID NO 50
<211> LENGTH: 18
<212> TYPE: DNA
<213> ORGANISM: Homo sapiens

<400> SEQUENCE: 50
ttggagctgg tggcgtag                                            18

<210> SEQ ID NO 51
<211> LENGTH: 19
<212> TYPE: DNA
<213> ORGANISM: Homo sapiens

<400> SEQUENCE: 51
atcttatccg agtggaagg                                           19

<210> SEQ ID NO 52
<211> LENGTH: 18
```

```
<212> TYPE: DNA
<213> ORGANISM: Homo sapiens

<400> SEQUENCE: 52
cctgcatggg cggcatga                                                 18

<210> SEQ ID NO 53
<211> LENGTH: 18
<212> TYPE: DNA
<213> ORGANISM: Homo sapiens

<400> SEQUENCE: 53
ctctcccagg acaggcac                                                 18

<210> SEQ ID NO 54
<211> LENGTH: 18
<212> TYPE: DNA
<213> ORGANISM: Homo sapiens

<400> SEQUENCE: 54
cttcaaagcg aggtttgc                                                 18

<210> SEQ ID NO 55
<211> LENGTH: 18
<212> TYPE: DNA
<213> ORGANISM: Homo sapiens

<400> SEQUENCE: 55
gaaacaaatc gagtgggt                                                 18

<210> SEQ ID NO 56
<211> LENGTH: 18
<212> TYPE: DNA
<213> ORGANISM: Homo sapiens

<400> SEQUENCE: 56
cagtgtcaca gcacccta                                                 18

<210> SEQ ID NO 57
<211> LENGTH: 19
<212> TYPE: DNA
<213> ORGANISM: Homo sapiens

<400> SEQUENCE: 57
ccaccacctc ctcaaacag                                                19

<210> SEQ ID NO 58
<211> LENGTH: 20
<212> TYPE: DNA
<213> ORGANISM: Homo sapiens

<400> SEQUENCE: 58
gaggcagaaa aaactattga                                               20

<210> SEQ ID NO 59
<211> LENGTH: 18
<212> TYPE: DNA
<213> ORGANISM: Homo sapiens

<400> SEQUENCE: 59
cgagatttca ctgtagct                                                 18

<210> SEQ ID NO 60
<211> LENGTH: 20
```

-continued

```
<212> TYPE: DNA
<213> ORGANISM: Homo sapiens

<400> SEQUENCE: 60
gtaatacgac tcactatagg                                              20
```